(12) United States Patent
Carpenter et al.

(10) Patent No.: US 8,163,269 B2
(45) Date of Patent: *Apr. 24, 2012

(54) BIOACTIVE STENTS FOR TYPE II DIABETICS AND METHODS FOR USE THEREOF

(76) Inventors: Kenneth W. Carpenter, San Diego, CA (US); William G. Turnell, San Diego, CA (US); Kristin M. DeFife, San Diego, CA (US); Kathryn A. Grako, San Diego, CA (US)

( * ) Notice: Subject to any disclaimer, the term of this patent is extended or adjusted under 35 U.S.C. 154(b) by 1358 days.

This patent is subject to a terminal disclaimer.

(21) Appl. No.: 11/098,891

(22) Filed: Apr. 4, 2005

(65) Prior Publication Data

US 2005/0238689 A1 Oct. 27, 2005

Related U.S. Application Data

(60) Provisional application No. 60/559,937, filed on Apr. 5, 2004.

(51) Int. Cl.
*A61M 36/14* (2006.01)
*A61K 51/00* (2006.01)

(52) U.S. Cl. ............... 424/1.69; 424/1.11; 424/1.65; 424/9.1; 514/1.1

(58) Field of Classification Search ............ 424/1.11, 424/1.49, 1.65, 1.69, 1.73, 9.1, 9.2, 9.3, 9.4, 424/9.5, 9.6, 9.7, 9.8; 206/223, 569, 570; 514/1.1

See application file for complete search history.

(56) References Cited

U.S. PATENT DOCUMENTS

| | | | |
|---|---|---|---|
| 5,591,227 A | 1/1997 | Dinh et al. | |
| 5,929,893 A | 7/1999 | Son et al. | 347/255 |
| 6,503,538 B1 | 1/2003 | Chu et al. | |
| 6,703,040 B2 | 3/2004 | Katsarava et al. | 424/444 |
| 6,982,249 B1 | 1/2006 | Schmaier et al. | |
| 7,041,785 B1 | 5/2006 | Recoli et al. | |
| 2002/0049495 A1 | 4/2002 | Kutryk et al. | |
| 2002/0106369 A1 | 8/2002 | Horvath et al. | 424/131.1 |
| 2003/0064053 A1 | 4/2003 | Liu et al. | 424/85.2 |
| 2003/0215454 A1 | 11/2003 | Colb et al. | |
| 2003/0229393 A1 | 12/2003 | Kutryk et al. | |
| 2004/0170685 A1 | 9/2004 | Carpenter et al. | |
| 2005/0025752 A1 | 2/2005 | Kutryk et al. | |
| 2005/0043787 A1 | 2/2005 | Kutryk et al. | |
| 2005/0271700 A1 | 12/2005 | DesNoyer et al. | 424/426 |
| 2005/0271701 A1 | 12/2005 | Cottone, Jr. et al. | |
| 2006/0074191 A1 | 4/2006 | DesNoyer et al. | 525/178 |
| 2006/0111546 A1 | 5/2006 | Pacetti et al. | 528/190 |
| 2006/0121012 A1 | 6/2006 | Kutryk et al. | |
| 2006/0135476 A1 | 6/2006 | Kutryk et al. | |
| 2007/0042017 A1 | 2/2007 | Kutryk et al. | |
| 2007/0055367 A1 | 3/2007 | Kutryk et al. | |
| 2007/0141107 A1 | 6/2007 | Kutryk et al. | |
| 2007/0156232 A1 | 7/2007 | Kutryk et al. | |
| 2007/0191932 A1 | 8/2007 | Kutryk et al. | |
| 2007/0196422 A1 | 8/2007 | Kutryk et al. | |
| 2007/0213801 A1 | 9/2007 | Kutryk et al. | |

FOREIGN PATENT DOCUMENTS

WO WO 03/062298 A1 7/2003

OTHER PUBLICATIONS

"Clinical Trial to Prevent Restenosis", *JACC*, pp. 59A (1994).
Ferns et al., "Inhibition of Neointimal Smooth Muscle Accumulation After Angioplasty by an Antibody to PDGF", *Science*, vol. 253: pp. 1129-1132 (1991).
Furchgott and Zawadzki, "The obligatory role of endothelial cells in the relaxation of arterial smooth muscle by acetylcholine", *Nature*, vol. 288: pp. 373-376 (1980).
Garg and Hassid, "Nitric Oxide-generating Vasodilators and 8-Bromo-Cyclic Guanosine Monophosphate Inhibit Mitogenesis and Proliferation of Cultured Rat Vascular Smooth Muscle Cells", *J. Clin. Invest.*, vol. 83: pp. 1774-1777 (1989).
Gehling et al., "In vitro differentiation of endothelial cells from AC133-positive progenitor cells", *Blood*, vol. 95, No. 10: pp. 3106-3112 (2000).
Gill et al., "Vascular Trauma Induces Rapid but Transient Mobilization of VEGFR2$^+$AC133$^+$ Endothelial Precursor Cells", *Circulation Research*, vol. 88: pp. 167-174 (2001).
Hristov et al., "Endothelial Progenitor Cells, Mobilization, Differentiation, and Homing", *Arterioscler Thromb Vasc Biol.*, vol. 23: pp. 1185-1189 (2003).
Lundell et al., "Activation of β integrins on CML progenitors reveals cooperation between β integrins and CD44 in the regulation of adhesion and proliferation", *Leukemia*, vol. 11: pp. 822-829 (1997).
Moncada et al., "Nitric Oxide: Physiology, Pathophysiology, and Pharmacology", *Pharmacological Reviews*, vol. 43, No. 2: pp. 109-142 (1991).
Myers et al., "Vasorelaxant properties of the endothelium-derived relaxing factor more closely resemble S-nitrosocysteine than nitric oxide", *Nature*, vol. 345: pp. 161-163 (1990).
Peichev et al., "Expression of VEGFR-2 and AC133 by circulating human CD34+ cells identifies a population of functional endothelial precursors", *Blood*, vol. 95, No. 3: pp. 952-958 (2000).
Radomski et al., "Comparative pharmacology of endothelium-derived relaxing factor, nitric oxide and prostacyclin in platelets", *Br. J. Pharmac.*, vol. 92: pp. 181-187 (1987).
Schofield et al., "The Effect of $a_4\beta_1$-Integrin Binding Sequences of Fibronectin on Growth of Cells From Human Hematopoietic Progenitors", *Blood*, vol. 91, No. 9: pp. 3230-3238 (1998).
Urbich and Dimmeler, "Endothelial Progenitor Cells Characterization and Role in Vascular Biology", *Circulation Research*, vol. 95: pp. 343-353 (2004).
Dekker A. et ai., "Improved Adhesion and Proliferation of Human Endothelial Cells on Polyethylene Precoated with Monoclonal Antibodies Directed Against Cell Membrane Antigens and Extracellular Matrix Proteins," *Journal of the International Society on Thrombosis and Haemostasis*, Dec 2, 1991, pp. 715-724, vol. 66, No. 6, New York, U.S.A.

*Primary Examiner* — D L Jones

(57) ABSTRACT

The present invention is based on the discovery that a vascular stent or other implantable medical device can be coated with a biodegradable biocompatible polymer to which is attached a bioligand that specifically captures progenitors of endothelial cells (PECs) from the circulating blood to promote endogenous formation of healthy endothelium in Type II diabetics. In one embodiment, the bioligand is a peptide that specifically binds to an integrin receptor on PECs. The invention also provides methods for using such vascular stents and other implantable devices to promote vascular healing in Type II diabetics, for example following mechanical intervention.

41 Claims, 6 Drawing Sheets

```
                        SEQUENCE LISTING

<160> NUMBER OF SEQ ID NOS: 11

<210> SEQ ID NO 1
<211> LENGTH: 20
<212> TYPE: PRT
<213> ORGANISM: Artificial sequence
<220> FEATURE:
<223> OTHER INFORMATION: Synthetic construct

<400> SEQUENCE: 1

Gly Glu Glu Ile Gln Ile Gly His Ile Pro Arg Glu Asp Val Asp Tyr
1               5                   10                  15

His Leu Tyr Pro
            20

<210> SEQ ID NO 2
<211> LENGTH: 6
<212> TYPE: PRT
<213> ORGANISM: Artificial sequence
<220> FEATURE:
<223> OTHER INFORMATION: Synthetic construct

<400> SEQUENCE: 2

Arg Glu Asp Val Asp Tyr
1               5

<210> SEQ ID NO 3
<211> LENGTH: 61
<212> TYPE: PRT
<213> ORGANISM: Artificial sequence
<220> FEATURE:
<223> OTHER INFORMATION: Small bacterial proteinaceous motif

<400> SEQUENCE: 3

Met Thr Pro Ala Val Thr Thr Tyr Lys Leu Val Ile Asn Gly Lys Thr
1               5                   10                  15

Leu Lys Gly Glu Thr Thr Thr Lys Ala Val Asp Ala Glu Thr Ala Glu
            20                  25                  30

Lys Ala Phe Lys Gln Tyr Ala Asn Asp Asn Gly Val Asp Gly Val Trp
        35                  40                  45

Thr Tyr Asp Asp Ala Thr Lys Thr Phe Thr Val Thr Glu
    50                  55                  60

<210> SEQ ID NO 4
<211> LENGTH: 55
<212> TYPE: PRT
<213> ORGANISM: Artificial sequence
<220> FEATURE:
<223> OTHER INFORMATION: Small bacterial proteinaceous motif

<400> SEQUENCE: 4

Thr Tyr Lys Leu Ile Leu Asn Gly Lys Thr Leu Lys Gly Glu Thr Thr
1               5                   10                  15

Thr Glu Ala Val Asp Ala Ala Thr Ala Glu Lys Val Phe Lys Gln Tyr
```

20                  25                  30

Ala Asn Asp Asn Gly Val Asp Gly Glu Trp Thr Tyr Asp Asp Ala Thr
            35                  40                  45

Lys Thr Phe Thr Val Thr Glu
        50                  55

<210> SEQ ID NO 5
<211> LENGTH: 61
<212> TYPE: PRT
<213> ORGANISM: Artificial sequence
<220> FEATURE:
<223> OTHER INFORMATION: Small bacterial proteinaceous motif

<400> SEQUENCE: 5

Met Thr Pro Ala Val Thr Thr Tyr Lys Leu Val Ile Asn Gly Lys Thr
1               5                   10                  15

Leu Lys Gly Glu Thr Thr Thr Lys Ala Val Asp Ala Glu Thr Ala Glu
                20                  25                  30

Lys Ala Phe Lys Gln Tyr Ala Asn Asp Asn Gly Val Asp Gly Val Trp
            35                  40                  45

Thr Tyr Asp Asp Ala Thr Lys Thr Phe Thr Val Thr Glu
        50                  55                  60

<210> SEQ ID NO 6
<211> LENGTH: 55
<212> TYPE: PRT
<213> ORGANISM: Artificial sequence
<220> FEATURE:
<223> OTHER INFORMATION: Synthetic peptide

<400> SEQUENCE: 6

Thr Tyr Lys Leu Ile Leu Asn Gly Lys Thr Leu Lys Gly Glu Thr Thr
1               5                   10                  15

Thr Glu Ala Val Asp Ala Ala Thr Ala Glu Lys Val Phe Lys Gln Tyr
                20                  25                  30

Ala Asn Asp Asn Gly Val Asp Gly Glu Trp Thr Tyr Asp Asp Ala Thr
            35                  40                  45

Lys Thr Phe Thr Val Thr Glu
        50                  55

<210> SEQ ID NO 7
<211> LENGTH: 10
<212> TYPE: PRT
<213> ORGANISM: Artificial sequence
<220> FEATURE:
<223> OTHER INFORMATION: Small proteinaceous motif

<400> SEQUENCE: 7

Lys Arg Pro Pro Gly Phe Ser Pro Phe Arg
1               5                   10

<210> SEQ ID NO 8
<211> LENGTH: 9
<212> TYPE: PRT
<213> ORGANISM: Artificial sequence
<220> FEATURE:
<223> OTHER INFORMATION: Small proteinaceous motif

<400> SEQUENCE: 8

Lys Arg Pro Pro Gly Phe Ser Pro Phe
1               5

<210> SEQ ID NO 9

```
<211> LENGTH: 9
<212> TYPE: PRT
<213> ORGANISM: Artificial sequence
<220> FEATURE:
<223> OTHER INFORMATION: Small proteinaceous motif

<400> SEQUENCE: 9

Arg Pro Pro Gly Phe Ser Pro Phe Arg
1               5

<210> SEQ ID NO 10
<211> LENGTH: 8
<212> TYPE: PRT
<213> ORGANISM: Artificial sequence
<220> FEATURE:
<223> OTHER INFORMATION: Small proteinaceous motif

<400> SEQUENCE: 10

Arg Pro Pro Gly Phe Ser Pro Phe
1               5

<210> SEQ ID NO 11
<211> LENGTH: 7
<212> TYPE: PRT
<213> ORGANISM: Artificial sequence
<220> FEATURE:
<223> OTHER INFORMATION: Synthetic construct

<400> SEQUENCE: 11

Gly Arg Glu Asp Val Asp Tyr
1               5
```

BIOACTIVE STENTS FOR TYPE II DIABETICS AND METHODS FOR USE THEREOF

RELATED APPLICATION

This application relies for priority under 35 U.S.C. §119(e) upon U.S. Provisional Application Ser. No. 60/559,937 filed Apr. 5, 2004.

FIELD OF THE INVENTION

The invention relates generally to implantable medical devices, and in particular to biodegradable polymer coated implantable stents that promote vascular healing in diabetics.

BACKGROUND INFORMATION

The normal endothelium, which lines blood vessels, is uniquely and completely compatible with blood. Endothelial cells initiate metabolic processes, like the secretion of prostacyclin and endothelium-derived relaxing factor (EDRF), which actively discourage platelet deposition and thrombus formation in vessel walls. However, damaged arterial surfaces within the vascular system are highly susceptible to thrombus formation. Abnormal platelet deposition, resulting in thrombosis, is more likely to occur in vessels in which endothelial, medial and adventitial damage has occurred. While systemic drugs have been used to prevent coagulation and to inhibit platelet aggregation, a need exists for a means by which a damaged vessel can be treated directly to prevent thrombus formation and subsequent intimal smooth muscle cell proliferation.

Current treatment regimes for stenosis or occluded vessels include mechanical interventions. However, these techniques exacerbate the injury, precipitating new smooth muscle cell proliferation and neointimal growth. For example, stenotic arteries are often treated with balloon angioplasty, which involves the mechanical dilation of a vessel with an inflatable catheter. The effectiveness of this procedure is limited in some patients because the treatment itself damages the vessel, thereby inducing proliferation of smooth muscle cells and reocclusion or restenosis of the vessel. It has been estimated that approximately 30 to 40 percent of patients treated by balloon angioplasty and/or stents may experience restenosis within one year of the procedure. Damage to the endothelial and medial layers of a blood vessel, such as often occurs in the course of balloon angioplasty and stent procedures, has been found to stimulate neointimal proliferation, leading to restenosis of atherosclerotic vessels.

To overcome these problems, numerous approaches have been taken to providing stents useful in the repair of damaged vasculature. In one aspect, the stent itself reduces restenosis in a mechanical way by providing a larger lumen. For example, some stents gradually enlarge over time. To prevent damage to the lumen wall during implantation of the stent, many stents are implanted in a contracted form mounted on a partially expanded balloon of a balloon catheter and then expanded in situ to contact the lumen wall. U.S. Pat. No. 5,059,211 discloses an expandable stent for supporting the interior wall of a coronary artery wherein the stent body is made of a porous bioabsorbable material. To aid in avoiding damage to vasculature during implant of such stents, U.S. Pat. No. 5,662,960 discloses a friction-reducing coating of commingled hydrogel suitable for application to polymeric plastic, rubber or metallic substrates that can be applied to the surface of a stent.

A number of agents that affect cell proliferation have been tested as pharmacological treatments for stenosis and restenosis in an attempt to slow or inhibit proliferation of smooth muscle cells. These compositions have included heparin, coumarin, aspirin, fish oils, calcium antagonists, steroids, prostacyclin, ultraviolet irradiation, and others. Such agents may be systemically applied or may be delivered on a more local basis using a drug delivery catheter or a drug eluting stent. In particular, biodegradable polymer matrices loaded with a pharmaceutical may be implanted at a treatment site. As the polymer degrades, a medicament is released directly at the treatment site. The rate at which the drug is delivered is to a significant extent dependent upon the rate at which the polymer matrix is resorbed by the body. U.S. Pat. No. 5,342,348 to Kaplan and U.S. Pat. No. 5,419,760 to Norciso are exemplary of this technology. U.S. Pat. No. 5,766,710 discloses a stent formed of composite biodegradable polymers of different melting temperatures.

Porous stents formed from porous polymers or sintered metal particles or fibers have also been used for release of therapeutic drugs within a damaged vessel, as disclosed in U.S. Pat. No. 5,843,172. However, tissue surrounding a porous stent tends to infiltrate the pores. In certain applications, pores that promote tissue ingrowth are considered to be counterproductive because the growth of neointima can occlude the artery, or other body lumen, into which the stent is being placed.

Delivery of drugs to the damaged arterial wall components has also been explored by using latticed intravascular stents that have been seeded with sheep endothelial cells engineered to secrete a therapeutic protein, such as t-PA (D. A. Dichek et al., *Circulation*, 80:1347-1353, 1989). However, endothelium is known to be capable of promoting both coagulation and thrombolysis.

To prevent neointimal proliferation that leads to stenosis or restenosis, U.S. Pat. No. 5,766,584 to Edelman et al. describes a method for inhibiting vascular smooth muscle cell proliferation following injury to the endothelial cell lining by creating a matrix containing endothelial cells and surgically wrapping the matrix about the tunica adventitia. The matrix, and especially the endothelial cells attached to the matrix, secrete products that diffuse into surrounding tissue, but do not migrate to the endothelial cell lining of the injured blood vessel.

In a healthy individual in response to endothelial damage, the vascular endothelium participates in many homeostatic mechanisms important for normal wound healing, the regulation of vascular tone and the prevention of thrombosis. A primary mediator of these functions is endothelium-derived relaxing factor (EDRF). First described in 1980 by Furchgott and Zawadzki (Furchgott and Zawadzki, *Nature* (Lond.) 288: 373-376, 1980) EDRF is either nitric oxide (Moncada et al., *Pharmacol Rev.* 43:109-142, 1991.) (NO) or a closely related NO-containing molecule (Myers et al., *Nature* (Lond.), 345: 161-163, 1990).

Removal or damage to the endothelium is a potent stimulus for neointimal proliferation, a common mechanism underlying the restenosis of atherosclerotic vessels after balloon angioplasty. (Liu et al., *Circulation*, 79:1374-1387, 1989); (Fems et al., *Science*, 253:1129-1132, 1991). Stent-induced restenosis is caused by local wounding of the luminal wall of the artery. Further, restenosis is the result of a chronically-stimulated wound-healing cycle.

The natural process of wound healing involves a two-phase cycle: blood coagulation and inflammation at the site of the wound. In healthy individuals, these two cycles are counterbalanced, each including a natural negative feedback mechanism that prevents over-stimulation. For example, in the coagulation enzyme pathway thrombin factor Xa operates upon factor VII to control thrombus formation and, at the same time stimulates production of PARs (Protease Activated Receptors) by pro-inflammatory monocytes and macrophages. Nitric oxide produced endogenously by endothelial cells regulates invasion of the proinflammatory monocytes and macrophages. In the lumen of an artery, this two-phase cycle results in influx and proliferation of healing cells through a break in the endothelium. Stabilization of the vascular smooth muscle cell population by this naturally counterbalanced process is required to prevent neointimal proliferation leading to restenosis. The absence or scarcity of endogenously produced nitric oxide caused by damage to the endothelial layer in the vasculature is thought to be responsible for the proliferation of vascular smooth muscle cells that results in restenosis following vessel injury, for example following angioplasty.

Nitric oxide dilates blood vessels (Vallance et al., Lancet, 2:997-1000, 1989), inhibits platelet activation and adhesion (Radomski et al., Br. J Pharmacol, 92:181-187, 1987) and, in vitro, nitric oxide limits the proliferation of vascular smooth muscle cells (Garg et al., J. Clin. Invest. 83:1774-1777, 1986). Similarly, in animal models, suppression of platelet-derived mitogens by nitric oxide decreases intimal proliferation (Fems et al., Science, 253:1129-1132, 1991). The potential importance of endothelium-derived nitric oxide in the control of arterial remodeling after injury is further supported by recent preliminary reports in humans suggesting that systemic NO donors reduce angiographic-restenosis six months after balloon angioplasty (The ACCORD Study Investigators, J. Am. Coll. Cardiol. 23:59A. (Abstr.), 1994).

The earliest understanding of the function of the endothelium within an artery was its action as a barrier between highly reactive, blood borne materials and the intima of the artery. A wide variety of biological activity within the artery wall is generated when platelets, monocytes and neutrophils infiltrate intima. These reactions result from release of activating factors such as ATP and PDGF from platelets and IL-1, IL-6, TNFa and bFGF from monocytes and neutrophils. An important consequence of release of these activating factors is a change in the cellular structure of smooth muscle cells, causing the cells to shift from quiescent to migratory. This cellular change is of particular importance in vascular medicine, since activation of quiescent smooth muscle cells in arteries can lead to uncontrolled proliferation, leading to the blockage or narrowing of arteries known as stenosis or restenosis.

The standard of care for the non-surgical treatment of blocked arteries is to re-open the blockage with an angioplasty balloon, often followed by the placement of a wire metal structure called a stent to retain the opening in the artery. An unfortunate consequence of this procedure is the nearly total destruction of the endothelial layer by expansion of the angioplasty balloon and precipitation of a foreign body inflammatory response to the stent. Therefore, after removal of the balloon catheter used in the angioplasty, the artery is rapidly exposed to an influx of activating factors. Since mechanical intervention has destroyed the natural blood/artery barrier, in a significant number of patients the result is a local uncontrolled proliferative response by smooth muscle cells leading to restenosis.

A disproportionate number of diabetic patients, especially those with Type II diabetes, do not benefit from stenting of atherosclerotic arteries to the same extent as in equivalent non-diabetic patients. Clinical research has strongly implicated the generally impaired healing of the endothelium in patients who suffer from diabetes mellitus as a major contributor to the diminished therapeutic outcome in these patients when an arterial stent has been implanted. Impaired glucose tolerance (IGT) is considered a transitional phase to the development of Type II diabetes and many of the changes in health of endothelium found in Type II diabetics are prefigured in IGT. IGT and diabetes are also independently associated with the occurrence of cardiovascular disease. While Type II diabetic patients make up a significant proportion of those patients who experience such treatment failure, all Type II diabetics do not experience stent failure and the reason why some do and some do not has not hitherto been studied.

Thus, a need exists in the art for new and better methods and devices for stimulating and supplementing endothelial healing in patients who suffer from diabetes mellitus and who have suffered damage to arterial endothelial lining. Particularly, the need exists for better methods and devices for restoring in diabetics the natural process of wound healing in damaged arteries and other blood vessels.

SUMMARY OF THE INVENTION

The present invention is based on the discovery that endogenous endothelial healing processes at a site of vascular damage in patients suffering from Type II diabetes can be promoted by coating stents and other implantable devices with biodegradable, bioactive polymers bearing covalently attached bioligands that specifically capture and activate therapeutic progenitors of endothelial cells from the circulating blood of such patients. The polymers, which biodegrade over time, may also release bioactive agents that re-establish in patients suffering from Type II diabetes the natural endothelial healing process in an artery. The bioactive agent(s) attached to the polymers (e.g., the polymer backbone) promote endogenous endothelial processes in arteries of diabetics by specifically recruiting to the stent surface progenitors of endothelial cells from circulating blood at the site of stent or device implantation in the vasculature. Thus, a significant proportion of the healing properties of the stent in type II diabetics takes place before biodegradation of the stent.

In one embodiment, the invention provides bioactive implantable stents including a stent structure with a surface coating of a biodegradable, bioactive polymer, and at least one bioligand that specifically binds to an integrin receptor on progenitors of endothelial cells (PECs) in circulating blood. The bioligand is covalently bonded to the polymer. This bioligand may itself be bioactive in also activating the PECs, or it may act in conjunction with another bioactive PEC-activating agent.

In still another embodiment, the invention provides a kit that includes a biocompatible implantable stent. The invention stent has a stent structure with a surface coating of a biodegradable, biocompatible polymer with at least one bioligand or first member of a specific binding pair that binds specifically to an integrin receptor on PECs. The bioligand or first member is covalently bound to the biodegradable, biocompatible polymer.

In yet another embodiment, the invention provides a tubular sheath comprising a biodegradable, bioactive polymer, wherein the polymer comprises at least one bioligand covalently bound to the polymer, wherein the bioligand specifically binds to an integrin receptor on PECs in peripheral blood.

In another embodiment, the invention provides implantable medical devices having a biodegradable, bioactive polymer coated upon at least a portion of a surface. At least one bioligand that specifically binds an integrin receptor on PECs found in peripheral blood is covalently bound to the polymer.

In still another embodiment, the invention provides methods for treating damaged arterial endothelium in heart or limb in a patient having Type II diabetes comprising implanting an invention stent to promote natural healing of damaged endothelium in the artery wall of the patient.

In yet another embodiment, the invention provides methods for using a polymer as a medical device, a pharmaceutical, or as a carrier for covalent immobilization of a bioligand or first member of a specific binding pair that specifically attaches to an integrin receptor in PECs in the circulating blood of a patient with Type II diabetes into which the polymer is implanted. In this embodiment, a) the bioligand is a polypeptide that binds specifically to an integrin receptor on PECs in circulating blood; b) the bioligand forms a specific binding pair with an antibody that binds specifically to the integrin receptor; or c) the antibody is tagged with a first member of a specific binding pair and the bioligand comprises a second member of the specific binding pair.

In still another embodiment, the invention provides methods for promoting natural healing of endothelium damaged by mechanical intervention in an artery of a subject having Type II diabetes by implanting into the artery following the mechanical intervention an invention stent to promote natural healing of the artery.

BRIEF DESCRIPTION OF THE FIGURES

FIG. 6A shows a flowchart of the surface chemistry for conjugation of peptides to the acid version of the polymers (PEA-H). FIG. 6B shows a flowchart of the protocol for surface conjugation of peptides to mixtures of PEA polymers.

DETAILED DESCRIPTION OF THE INVENTION

Figure 1:
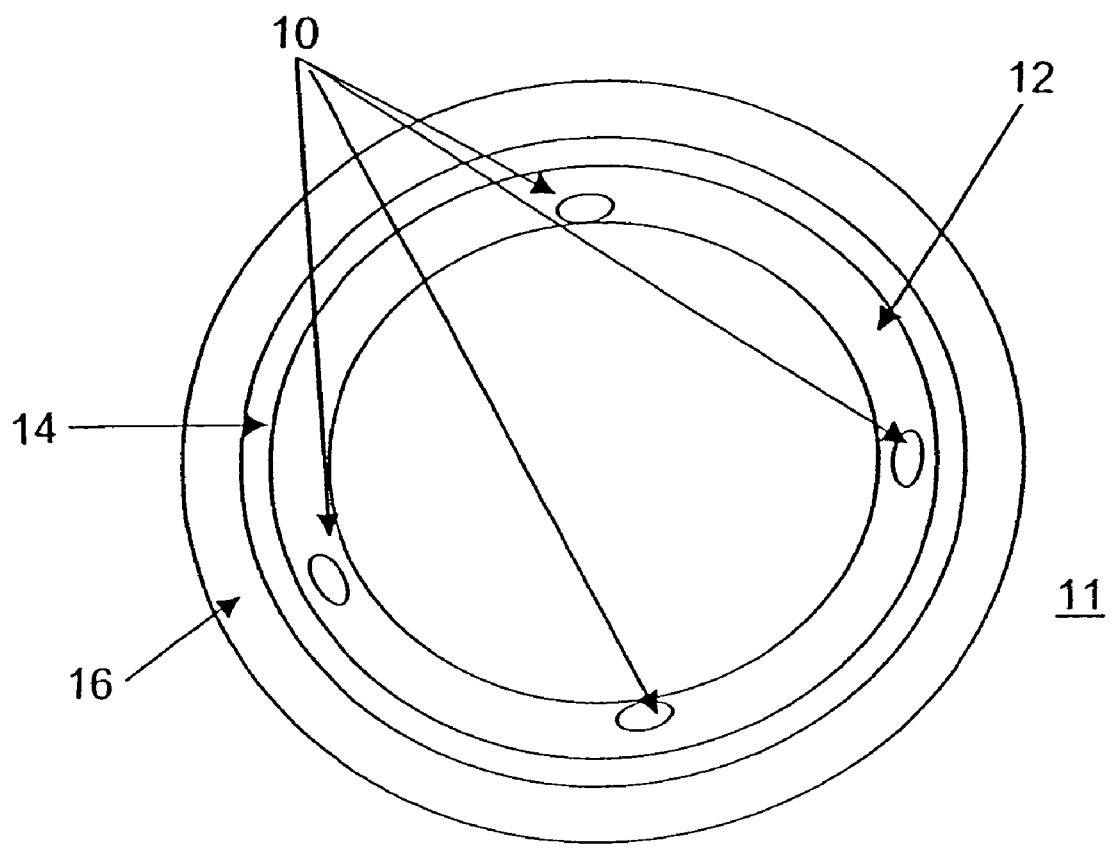
FIG. 1 is a schematic cross-section of an invention multi-layered polymer-coated stent.

In one embodiment, this invention provides stents and methods using such devices to re-establish an endothelial blood/artery barrier in patients suffering from diabetes mellitus, particularly Type II diabetes. The invention is also designed to promote endothelial healing at a site of damaged vascular endothelium in patients having impaired glucose tolerance, which is considered a transitional phase to the development of Type II diabetes. The invention stents comprise a biocompatible, resorbable polymeric sheath that encapsulates the stent structure. In a preferred embodiment of the invention methods, the stent is placed at the conclusion of an angioplasty procedure, or other medical procedure that damages arterial endothelium, without allowing a lapse of time sufficient for infiltration of inflammatory factors from the blood stream into the artery wall. In this method, the stent is placed at the location of the damage and preferably immediately covers and protects the area of damaged endothelium so as to prevent infiltration of inflammatory factors from the blood stream into the artery wall, while performing its primary function of gathering therapeutic progenitors of endothelial cells from the patient's circulating blood so that the natural processes of endothelial healing can go forward in the patient suffering from Type II diabetes.

In other words, the invention stents perform as an artificial endothelial layer while promoting the natural cycle of endothelial healing in diabetics as described herein. The polymeric sheath may have additional features that contribute to the healing of the artery. In one embodiment, the invention sheath or covering comprises multiple layers, each of which can perform a distinct function in re-establishing a stable lesion and contributing to healing endothelium of the injured artery wall.

The terms "diabetes" and "diabetes mellitus" as used herein mean Type II diabetes as well as impaired glucose tolerance (IGT), which is widely considered a transitional phase to the development of Type II diabetes. Many of the changes in health of endothelium found in Type II diabetics are prefigured in IGT.

The term "progenitors of endothelial cells (PECs)", as used herein with reference to the blood of subjects with Type II diabetes, encompasses, but is not limited to, endothelial progenitor cells (EPCs). There is significant evidence in the literature that endothelial progenitor cells (EPCs) can derive from the bone marrow and that CD133+/VEGFR2+ cells represent a population with endothelial progenitor capacity (*Blood* (2000) 95:952-958 and 3106-3112; *Circ. Res.* (2001) 88:167-174; *Arterioscler. Thromb. Vasc. Biol.* (2003) 23:1185-89 and *Circ. Res.* (2004) 95:343-353). There are, however, also reports of additional bone-marrow-derived cell populations (i.e. myeloid cells and mesenchymal cells) and even non-bone marrow-derived cells that can also give rise to endothelial cells (*Circulation* (2003) 107:1164-1169; *Circulation* (2003) 108:2511-2516; *Anat. Res.* (2004) Part A 276A: 13-21; and *Circ. Res.* (2004) 95:343-353). The more differentiated source of endothelial cells in the circulating blood may be monocytes or monocytic-like cells, and this is the source of PECs used in the Examples herein. The term "precursor endothelial cells" (PECs) is used herein to encompass and describe all of these non-"classical" precursors of ECs.

In another aspect, examples of bioligands suitable for use in capture of PECs from circulating blood are monoclonal antibodies directed against a known or identified surface marker of therapeutic PECs. Complementary determinants (CDs) that have been reported to decorate the surface of endothelial cells include CD31, CD34, CD102, CD105, CD106, CD109, CDw130, CD141, CD142, CD143, CD144, CDw145, CD146, CD147, and CD166. These cell surface markers can be of varying specificity for a particular cell/developmental type/stage in EC development. CDs 106, 142 and 144 have been reported to mark mature endothelial cells with some specificity. CD34 is presently known to be specific for progenitor endothelial cells in non-diabetics and therefore is one of the cell surface markers that is believed to be useful for capturing PECs out of blood circulating in the vessels in a diabetic patient into which the stent is implanted.

Additional examples of bioligands for the capture of PECs from circulating blood are extracellular matrix (ECM) proteins. Within the bone marrow stroma and in most areas of the body, interactions between progenitor cells and the ECM occur. ECM ligands are important, not only for differentiation and proliferation but also for maintenance of the hematopoietic stem cell. Fibronectin is one of the more ubiquitous members of the ECM. It is a potential ligand for most cell types and is recognized by at least 10 adhesion receptors of the integrin family (*Leukemia* 1997; 11:822-829 and *Blood* 1998; 91(9):3230-3238). In particular, CS5 and REDVDY are both found in the Type III connecting segment of fibronectin. The sequence for the CS5 peptide is: Gly-Glu-Glu-Ile-Gln-Ile-Gly-His-Ile-Pro-Arg-Glu-Asp-Val-Asp-Tyr-His-Leu-Tyr-Pro (SEQ ID NO:1), which contains REDVDY (underlined) (SEQ ID NO:2). It has been discovered that CS5 and REDVDY peptides bind specifically to integrin receptors on PECs.

The minimal active cell binding amino acid sequence, REDV, is somewhat related to the RGDs, a major active site in the central cell binding domain of fibronectin. However, REDV is novel in its cell type selectivity. The integrin α4β1 is known to bind to the REDV sequence and is found on ECs but not on SMCs (*JBC* (1991) 266(6):3579-3585; *Am. J of Pathology* (1994) 145:1070-1081; and *Blood* (1998) 91(9): 3230-32384). This becomes even more important in recruiting PECs versus smooth muscle progenitor cells (SPCs) in peripheral blood. Recent studies have shown that PECs express the α4β1 integrin while the SPCs do not (*Circ.* (2002) 106:1199-1204; and *Circ.* (2004) 110(17):2673-26775). This preference of REDV for ECs provides a significant advantage to a stent with a polymer coating containing REDV as a bioligand acting as a PEC cell recruitment factor. Even if an integrin receptor bioligand is not considered to significantly increase cell adhesion to the stent, it has been discovered that such bioligands still confer an advantage to the recruitment of ECs by stimulating more rapid adhesion with better cell spreading of ECs on stent surfaces.

The investigations into cell binding regions described in the Examples herein identified the importance of integrin receptors found on the surface of numerous cell types. Bioligands (e.g., peptides and polypeptides) that bind specifically to integrin receptors in PECs are incorporated into (e.g, covalently bonded to) a biodegradable polymer as described herein for coating at least a portion of the surface of an interventional implantable device, such as a vascular stent, to endow the coating with the property of preferential and specific recruitment of a subpopulation of PECs from the circulating bloodstream of a diabetic patient into which the device is implanted. The resulting localized concentration of PECs throughout the stent will enhance endothelial wound healing of the arterial wall of the diabetic patient.

In one embodiment, the bioligand is an antibody, such as a monoclonal antibody, and is specific for an integrin receptor identified on PECs as described above. A stent having a polymer coating to which the capture antibody is bound will, when implanted in a Type II diabetic, in turn bind to and hold captured PECs near the polymer surface for activation and subsequent migration.

As used herein, the term "antibody" is used in its broadest sense to include polyclonal and monoclonal antibodies, as well as antigen binding fragments of such antibodies. An antibody useful in a method of the invention, or an antigen-binding fragment thereof, is characterized, for example, by having specific binding activity for an epitope of a target molecule.

The antibody, for example, includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains (see Huse et al., *Science* 246:1275-1281 (1989)). These and other methods of making, for example, chimeric, humanized, CDR-grafted, single chain, and bifunctional antibodies are well known to those skilled in the art (Winter and Harris, *Immunol. Today* 14:243-246, 1993; Ward et al., *Nature* 341:544-546, 1989; Harlow and Lane, *Antibodies: A laboratory manual* (Cold Spring Harbor Laboratory Press, 1988); Hilyard et al., *Protein Engineering: A practical approach* (IRL Press 1992); Borrabeck, *Antibody Engineering*, 2d ed. (Oxford University Press 1995)). Examples of antibodies that can be used in the invention devices and methods include single-chain antibodies, chimeric antibodies, monoclonal antibodies, polyclonal antibodies, antibody fragments, Fab fragments, IgA, IgG, IgM, IgD, IgE and humanized antibodies. Monoclonal antibodies suitable for use as bioligands may also be obtained from a number of commercial sources. Such commercial antibodies are available against a wide variety of targets. Antibody probes can be conjugated to molecular backbones using standard chemistries, as discussed below.

The term "binds specifically" or "specific binding activity," when used in reference to an antibody means that an interaction of the antibody and a particular epitope has a dissociation constant of at least about $1 \times 10^{-6}$, generally at least about $1 \times 10^{-7}$, usually at least about $1 \times 10^{-8}$, and particularly at least about $1 \times 10^{-9}$ or $1 \times 10^{-10}$ or less. As such, Fab, F(ab')$_2$, Fd and Fv fragments of an antibody that retain specific binding activity for an epitope of an antigen, are included within the definition of an antibody.

In an alternative embodiment, a pair of biocompatible specific binding partners, A and B, can be used to specifically capture PECs from the circulating blood of Type II diabetics. In this embodiment, one of the specific binding pair acts as the bioligand covalently attached to the polymer coating of the stent or other implantable device. The other member of the pair of specific binding partners is attached or allowed to attach to an integrin receptor on the PECs of the diabetic patient to be treated (either ex vivo or in vivo by administration to the blood of the patient). For example, if the pair of biocompatible specific binding partners is biotin (molecule A) and streptavidin (molecule B), a Mab that binds specifically to a PEC cell surface marker, such as CD 144, can be conjugated with molecule A at a site on the Mab that does not interfere with the Mab binding to its cognate PEC cell surface marker. Alternatively, the roles of the specific binding partners, A and B, can be reversed, with biotin, for example, being attached to the polymer of the stent and streptavidin being attached to a monoclonal antibody administered to the patient for specific attachment to the integrin receptor on the patient's PECs.

In one embodiment of the invention, Mab-A conjugates are added to the patient's blood either in vivo (e.g., parenterally) or ex vivo (e.g., by extracorporeal circulation of the patient's blood) either prior to, contemporaneously with, or immediately following installation of the stent or other therapeutic device. As a result, circulating therapeutic EPC-Mab-A complexes are preferentially recruited to binding partner B, streptavidin, which is covalently attached to the device coating, enhancing the local concentration of therapeutic PECs at the site of intervention and injury. A monoclonal antibody administered to the blood of a human is preferably a "humanized monoclonal antibody" and suitable antigen-binding fragments can be commissioned commercially or can readily be produced recombinantly using well known techniques. Although this aspect of the invention is illustrated by reference to specific binding partners biotin and streptavidin, any biocompatible pair of specific binding partners can be used in an analogous way.

Alternatively, the biocompatible bioligand can further comprise one member of a specific binding pair, such as a biotin-streptavidin, and the other member of the specific binding pair can be pre-attached to the polymer. In use, in this alternative case, the bioligand is administered to the patient's blood stream, either in vivo or ex vivo, and allowed to bind to its specific target on therapeutic PECs therein, via a specific binding pair bridge. If the bioligand is administered to the patient's blood stream in vivo (e.g., parenterally), the PECs in the blood stream become bound to the polymer in vivo via the bioligand-specific binding pair-polymer complex.

In addition, small proteinaceous motifs, such as the B domain of bacterial Protein A and the functionally equivalent region of Protein G, are known to form a specific binding pair with, and thereby capture Fc-containing antibodies. Accordingly, in further embodiments, the antibody administered to the diabetic patient's blood is an Fc-containing antibody that is specific for an integrin receptor on PECs in blood and the bioligand attached to the polymer of the stent is a "sticky" peptide or polypeptide, such as Protein A and Protein G, which will capture the antibody and hold it near to the polymer surface of the stent to aid in recruiting PECs to the area of endothelium damage. However, these "sticky" peptides or polypeptides may also capture other circulating, Fc-containing, native antibodies, thereby reducing specificity of the reaction for the therapeutic purposes.

Protein A is a constituent of staphylococcus A bacteria that binds the Fc region of particular antibodies or immunoglobulin molecules. For example, the Protein A bioligand can be or contain the amino acid sequence:

(SEQ ID NO:3)
MTPAVTTYKLVINGKTLKGETTTKAVDAETAEKAFKQYANDNGVDGV

WTYDDATKTFTVTE or a functionally equivalent peptidic derivative thereof, such as, by way of an example, the functionally equivalent peptide or polypeptide having the amino acid sequence:

(SEQ ID NO:4)
TYKLILNGKTLKGETTTEAVDAATAEKVFKQYANDNGVDGEWTYDDAT

KTFTVTE

Protein G is a constituent of group G streptococci bacteria, and displays similar activity to Protein A, namely binding the Fc region of particular antibody or immunoglobulin molecules. For example, the Protein G bioligand can be, or contain Protein G having an amino acid sequence:

(SEQ ID NO:5)
MTPAVTTYKLVINGKTLKGETTTKAVDAETAEKAFKQYANDNGVDGVW

TYDDATKTFTVTE or a functionally equivalent peptide derivative thereof, such as, by way of an example, the functionally equivalent polypeptide having the amino acid sequence:

(SEQ ID NO:6)
TYKLILNGKTLKGETTTEAVDAATAEKVFKQYANDNGVDGEWTYDDAT

KTFTVTE

Such Protein A and Protein G molecules can be covalently attached as bioligands to the bioactive polymer coatings on the stent structure (e.g., the inner layer of a multilayered stent as described herein) and will act as bioligands to capture out of the patient's circulating blood stream Fc-containing antibodies that have been complexed with the patients' therapeutic PECs. Bioligands are selected and conjugated to the polymer backbone while avoiding steric hindrance to binding of the ligand to its biological target.

Other bioactive agents that activate the progenitor endothelial cells and are contemplated for attachment to the polymer backbone in the polymer coatings covering the invention medical devices (e.g., surface coatings of stents and sheaths for covering the stent structure) include the bradykinins. Bradykinins are vasoactive nonapeptides formed by the action of proteases on kininogens, to produce the decapeptide kallidin (KRPPGFSPFR) (SEQ ID NO:7), which can undergo further C-terminal proteolytic cleavage to yield the bradykinin 1 nonapeptide: (KRPPGFSPF) (SEQ ID NO: 8), or N-terminal proteolytic cleavage to yield the bradykinin 2 nonapeptide: (RPPGFSPFR) (SEQ ID NO: 9). Bradykinins 1 and 2 are functionally distinct as agonists of specific bradykinin cell surface receptors B1 and B2 respectively: both kallidin and bradykinin 2 are natural bioligands for the B2 receptor; whereas their C-terminal metabolites (bradykinin 1 and the octapeptide RPPGFSPF (SEQ ID NO:10) respectively) are bioligands for the B1 receptor. A portion of circulating bradykinin peptides can be subject to a further post-translational modification: hydroxylation of the second proline residue in the sequence (Pro3 to Hyp3 in the bradykinin 2 amino acid numbering). Bradykinins are very potent vasodilators, increasing permeability of post-capillary venules, and acting on endothelial cells to activate calmodulin and thereby nitric oxide synthase.

Bradykinin peptides are incorporated into the bioactive polymers used in the invention stents by attachment at one end of the peptide. The unattached end of the bradykinin extends freely from the polymer as a bioligand to contact endothelial cells in the vessel wall as well as progenitor endothelial cells captured from the blood in the vessel into which the stent is implanted. Thereby the endothelial cells with which contact is made become activated.

In a still further aspect, the bioactive agent can be a nucleoside, such as adenosine, which is also known to be a potent activator of endothelial cells to produce nitric oxide endogenously. Endothelial cells activated in this way activate further progenitor endothelial cells with which they come into contact. Thus, a cascade of endothelial cell activation at the site of the injury is caused to result in endogenous production of nitric oxide and development of an endothelial lining on the surface of the stent that contacts blood.

In another embodiment, the invention stent has a multilayered polymer covering that encapsulates a stent structure. FIG. 1 shows a schematic cross-section of an example of an invention stent 11 with stent struts 10 and a multilayered sheath or covering. When the multilayered stent is implanted, the outer layer 16 of the stent covering or sheath lies directly next to the artery wall. Bioactive agents and additional bioactive agents, as described herein, are incorporated into the outer layer of the stent covering or sheath to promote healing of the epithelium. An optional diffusion barrier layer 14 can be placed between and in contact with outer layer 16 and inner layer 12.

The inner layer 12 of the multilayered stent covering is exposed to the circulating blood with its PECs and has bioligands for recruitment of PECs covalently attached thereto. A biocompatible polymer of the type specifically described herein (e.g., having a chemical structure described by structures I and III herein) is used for inner layer 12. One or more bioligands that bind specifically to PECs, such as those having an amino acid sequence as set forth in SEQ ID NOS:1, 2, or 11, or a member of a specific binding pair for which the other member is contained within or conjugated with a specifically binding bioligand, are covalently attached to the polymer in the inner layer using techniques of covalent attachment described herein. For example, streptavidin can be bound to the polymer of the inner layer of the sheath for use with a biotin-tagged antibody that specifically binds the target on PECs in the circulating blood (which biotin-tagged antibody will be administered to the patient's blood stream). Optionally, one or more "bioactive agent," as described herein, but not "an additional bioactive agent" can also be covalently bound to the polymer in the inner layer of the multilayered stent. As in other embodiments of the invention stents, the bioactive agent is selected to activate PECs attracted to the inner layer of the sheath from the circulating blood of diabetic patients by the bioligands attached to the inner layer of the stent covering. Thus the stent takes an active role in the process of re-establishing the natural endothelial cell layer at the site of one or more damaged areas of arterial endothelium.

The outer layer 16 comprises a polymer layer loaded with a bioactive agent and/or an additional bioactive agent, or combination thereof, specifically including those that limit cellular proliferation or reduce inflammation as disclosed herein. These cellular proliferation limiting and/or inflammation reducing drugs and bioactive agents can be solubilized in the polymer solid phase and, hence, are preferably not bound to the polymer of the outer layer. Rather such bioactive agents and additional bioactive agents are loaded into the polymer and sequestered there until the stent is put into place. Once implanted, the bioactive agents in the outer layer 16 are eluted and diffuse into the artery wall.

Preferred bioactive agents for incorporation into the outer layer of invention multilayered stents include rapamycin and any of its analogs or derivatives, such as everolimus (also known as sirolimus), paclitaxel or any of its analogs or derivatives, and statins, such as simvastatin. In the outer layer, non-covalently bound bioactive agents and/or additional bioactive agents can be intermingled with or "loaded into" any biocompatible biodegradable polymer as is known in the art since the outer layer in this embodiment of the invention does not come into contact with blood, except during placement of the stent.

Optionally, lying along and covering the interior surface of the outer layer of the covering is a diffusion barrier layer 14 of resorbable polymer that acts as a diffusion barrier to the bioactive agent or additional bioactive agent contained in the outer layer. The purpose of this diffusion barrier is to direct elution of the drug/biologic into the artery wall to prevent proliferation of smooth muscle cells, while limiting or preventing passage of the drug/biologic into the inner layer. The diffusion barrier layer 14 can accomplish its purpose of partitioning of the drug through hydrophobic/hydrophilic interaction related to the solubility of the bioactive agent in the polymer solid phase. For example, if the bioactive agent or additional bioactive agent in the outer layer is hydrophobic, the polymer barrier layer is selected to be less hydrophobic than the agent(s), and if the bioactive agent or additional bioactive agent in the outer layer is hydrophilic, the barrier layer is selected to be hydrophobic. For example, the barrier layer can be selected from such polymers as polyester, poly (amino acid), poly(ester amide), poly(ester urethane), polyurethane, polylactone, poly(ester ether), or copolymers thereof, whose charge properties are well known by those of skill in the art. The barrier layer is considered optional because the inner layer of the stent may itself prove an effective diffusion barrier, depending upon the properties of the polymers and various active agents contained in the inner and outer layers of the stent.

In one embodiment, the stent structure used in manufacture of the invention multilayered stent as well as the stents comprising a single layer of polymer covering described herein is made of a biodegradable and absorbable material with sufficient strength and stiffness to replace a conventional stent structure, such as a stainless steel or wire mesh stent structure. A cross-linked poly(ester amide), polycaprolactone, or poly (ester urethane) as described herein can be used for this purpose so that the stent structure as well as its covering(s) is completely bioabsorbable, for example, over a period of three months to years. In this case, over time, each of the layers, and the stent structure as well, will be re-absorbed by the body through natural processes, including enzymatic action, allowing the re-established endothelial cell layer to resume its dual function of acting as a blood/artery barrier and providing natural control and stabilization of the intra-cellular matrix within the artery wall through the production of nitric oxide.

As used herein, "biodegradable" means that at least the polymer coating of the invention stent is capable of being broken down into innocuous and biocompatible products in the normal functioning of the body. In one embodiment, the entire stent, including the stent structure is biodegradable. The preferred biodegradable, biocompatible polymers have hydrolyzable ester and/or amide linkages, which provide the biodegradability, and are typically chain terminated with carboxyl or capping groups.

Biodegradable, blood compatible polymers suitable for use in the practice of the invention of the type specifically described herein (e.g., having a chemical structure described by structures I and III herein) bear functionalities that allow for facile covalent attachment of bioactive agents to the polymer. For example, a polymer bearing carboxyl groups can readily react with a bioactive agent having an amino moiety, thereby covalently bonding the bioactive agent to the polymer via the resulting amide group. As will be described herein, the biodegradable, biocompatible polymer and the bioligands and bioactive agents can contain numerous complementary functional groups that can be used to covalently attach the bioactive agent to the biodegradable, biocompatible polymer.

The term "bioactive agent", as used herein, means agents that play an active role in the endogenous healing processes at a site of stent implantation by holding bioligands or members of a specific binding pair, and/or releasing a bioactive or therapeutic agent during biodegradation of the polymer. Bioactive agents, include those specifically described herein as having properties that capture (i.e., "bioligands"), attract and activate captured circulating PECs, and are contemplated for covalent attachment to the polymers used in coating the invention stents. Such bioactive agents include, but are not limited to, agents that, when freed from the polymer backbone during polymer degradation, promote endogenous production of a therapeutic natural wound healing agent, such as nitric oxide endogenously produced by endothelial cells. Alternatively the "bioactive agents" released from the polymers during degradation may be directly active in promoting natural wound healing processes by endothelial cells while controlling proliferation of smooth muscle cells in the vessel at the locus of the damage. These bioactive agents can include any agent that donates, transfers, or releases nitric oxide, elevates endogenous levels of nitric oxide, stimulates endogenous synthesis of nitric oxide, or serves as a substrate for nitric oxide synthase or that inhibits proliferation of smooth muscle cells. Such agents include, for example, aminoxyls, furoxans, nitrosothiols, nitrates and anthocyanins; nucleosides such as adenosine, and nucleotides such as adenosine diphosphate (ADP) and adenosine triphosphate (ATP); neurotransmitter/neuromodulators such as acetylcholine and 5-hydroxytryptamine (serotonin/5-HT); histamine and catecholamines such as adrenalin and noradrenalin; lipid molecules such as sphingosine-1-phosphate and lysophosphatidic acid; amino acids such as arginine and lysine; peptides such as the bradykinins, substance P and calcium gene-related peptide (CGRP), and proteins such as insulin, vascular endothelial growth factor (VEGF), and thrombin.

A wide variety of other bioactive agents are optionally covalently attached to the bioactive polymers used in the coverings of the invention stents and devices. Aminoxyls contemplated for use as bioactive agents have the structure:

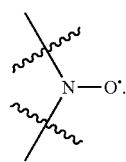

Exemplary aminoxyls include the following compounds:

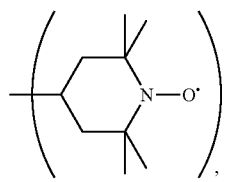
1

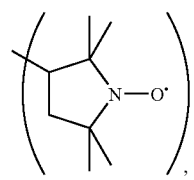
2

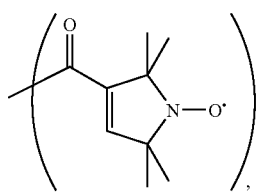
3

2,2,6,6-tetramethylpiperidine-1-oxy (1); 2,2,5,5-tetramethylpyrrolidine-1-oxy (2); and 2,2,5,5-tetramethylpyrroline-1-oxy-3-carbonyl (3). Further aminoxyls contemplated for use include 4-amino-2,2,6,6-tetramethylpiperidine-1-oxy (TEMPAMINE); 4-(N,N-dimethyl-N-hexadecyl)ammonium-2,2,6,6-tetramethylpiperidine-1-oxy, iodide (CAT 16); 4-(N,N-dimethyl-N-(2-hydroxyethyl))ammonium-2,2,6,6-tetramethylpiperidine-1-oxy(TEMPO choline); 4-(N,N-dimethyl-N-(3-sulfopropyl)ammonium-2,2,6,6-tetramethylpiperidine-1-oxy; N-(4-(iodoacetyl)amino-2,2,6,6-tetramethylpiperidine-1-oxy(TEMPO 1A); N-(2,2,6,6-tetramethylpiperidine-1-oxy4-yl)maleimide (TEMPO maleimide, MAL-6); and 4-trimethylammonium-2,2,6,6-tetramethylpiperidine-1-oxy, iodide (CAT 1); 3-amino-2,2,5,5-tetramethylpyrrolidine-1-oxy; and N-(3-(iodoacetyl)amino)-2,2,5,5-tetramethylpyrrolidine-1-oxy(PROXYL 1A); succinimidyl 2,2,5,5-tetramethyl-3-pyrroline-1-oxy-3-carboxylate and 2,2,5,5-tetramethyl-3-pyrroline-1-oxy-3-carboxylic acid, and the like.

Furoxans contemplated for use as bioactive agents have the structure:

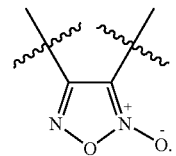

An exemplary furoxan is 4-phenyl-3-furoxancarbonitrile, as set forth below:

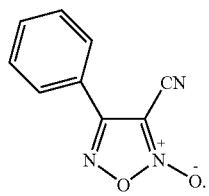

Nitrosothiols include compounds bearing the —S—N=O moiety, such as the exemplary nitrosothiol set forth below:

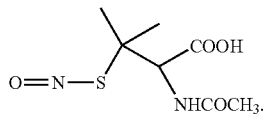

Anthocyanins are also contemplated for use as bioactive agents. Anthocyanins are glycosylated anthocyanidins and have the structure:

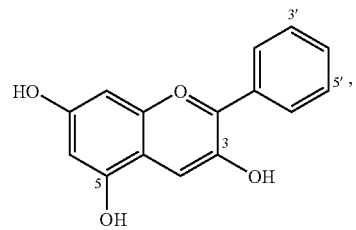

wherein the sugars are attached to the 3-hydroxy position. Anthocyanins are known to stimulate NO production in vivo and therefore are suitable for use as bioactive agents in the practice of the invention.

Bioactive agents for dispersion into and release from the surface coverings of the invention stents and medical devices also include anti-proliferants, rapamycin and any of its analogs or derivatives, paclitaxel or any of its taxene analogs or derivatives, everolimus, Sirolimus, tacrolimus, or any of its-limus named family of drugs, and statins such as simvastatin, atorvastatin, fluvastatin, pravastatin, lovastatin, rosuvastatin, geldanamycins, such as 17AAG (17-allylamino-17-demethoxygeldanamyc in); Epothilone D and other epothilones, 17-dimethylaminoethylamino-17-demethoxygeldanamycin and other polyketide inhibitors of heat shock protein 90 (Hsp90), Cilostazol, and the like.

Polymers contemplated for use in forming the blood-compatible, hydrophilic coating or inner layer in the invention multilayered stents include polyesters, poly(amino acids), polyester amides, polyurethanes, or copolymers thereof. In particular, examples of biodegradable polyesters include poly (α-hydroxy $C_1$-$C_5$ alkyl carboxylic acids), e.g., polyglycolic acids, poly-L-lactides, and poly-D,L-lactides; poly-3-hydroxy butyrate; polyhydroxyvalerate; polycaprolactones, e.g., poly(ϵ-caprolactone); and modified poly(α-hydroxy-acid)homopolymers, e.g., homopolymers of the cyclic diester monomer, 3-(S)[alkyloxycarbonyl)methyl]-1,4-dioxane-2,5-dione which has the formula 4 where R is lower alkyl, depicted in Kimura, Y., "Biocompatible Polymers" in *Biomedical Applications of Polymeric Materials*, Tsuruta, T., et al, eds., CRC Press, 1993 at page 179.

Examples of biodegradable copolymer polyesters useful in forming the blood-compatible, hydrophilic coating or inner layer in the invention stents include copolyester amides, copolyester urethanes, glycolide-lactide copolymers, glycolide-caprolactone copolymers, poly-3-hydroxy butyrate-valerate copolymers, and copolymers of the cyclic diester monomer, 3-(S)[(alkyloxycarbonyl)methyl]-1,4-dioxane-2,5-dione, with L-lactide. The glycolide-lactide copolymers include poly(glycolide-L-lactide) copolymers formed utilizing a monomer mole ratio of glycolic acid to L-lactic acid ranging from 5:95 to 95:5 and preferably a monomer mole ratio of glycolic acid to L-lactic acid ranging from 45:65 to 95:5. The glycolide-caprolactone copolymers include glycolide and ϵ-caprolactone block copolymer, e.g., Monocryl or Poliglecaprone.

The biodegradable polymers useful in forming the coatings for the invention biocompatible polymer coated stents and medical devices also include those comprising at least one amino acid conjugated to at least one non-amino acid moiety per repeat unit. The term "non-amino acid moiety" as used herein includes various chemical moieties, but specifically excludes amino acid derivatives and peptidomimetics as described herein. In addition, the polymers containing at least one amino acid are not contemplated to include poly(amino acid) segments, including naturally occurring polypeptides, unless specifically described as such. In one embodiment, the non-amino acid is placed between two adjacent amino acids in the repeat unit. The polymers may comprise at least two different amino acids per repeat unit.

Preferred for use in forming the biocompatible polymer surface coverings of the invention stents and medical devices (and the inner layers of invention multilayered stents) are polyester amides (PEAs) and polyester urethanes (PEURs) that have built-in functional groups on PEA or PEUR side chains, and these built-in functional groups can react with other chemicals and lead to the incorporation of additional functional groups to expand the functionality of PEA or PEUR further. Therefore, such polymers used in the invention compositions and methods are ready for reaction with other chemicals having a hydrophilic structure to increase water solubility and with bioactive agents and additional bioactive agents, without the necessity of prior modification.

In addition, the polymers used in the invention polymer coated stents and medical devices display minimal hydrolytic degradation when tested in a saline (PBS) medium, but in an enzymatic solution, such as chymotrypsin or CT, a uniform erosive behavior has been observed.

In one embodiment the PEAs and PEURs have a chemical formula described by the general structural formula (I):

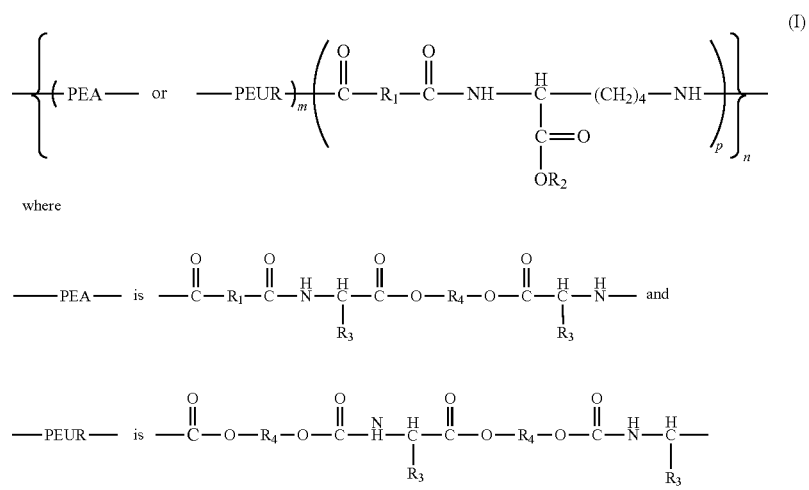

where and wherein n ranges from about 50 to about 150, m ranges about 0.1 to about 0.9: p ranges from about 0.9 to about 0.1; $R_1$ is selected from $(C_2$-$C_{20})$alkylene and $(C_2$-$C_{20})$alkenylene; $R_2$ is selected from hydrogen, $(C_6$-$C_{10})$aryl$(C_1$-$C_6)$ alkyl, t-butyl and other protecting group; $R_3$ is selected from hydrogen, $(C_1$-$C_6)$alkyl, $(C_2$-$C_6)$alkenyl, $(C_2$-$C_6)$alkynyl and $(C_6$-$C_{10})$aryl$(C_1$-$C_6)$alkyl; and $R_4$ is selected from $(C_2$-$C_{20})$ alkylene, $(C_2$-$C_{20})$alkenylene, $(C_2$-$C_{20})$alkyloxy, and bicyclic-fragments of 1,4:3,6-dianhydrohexitols of general formula (II):

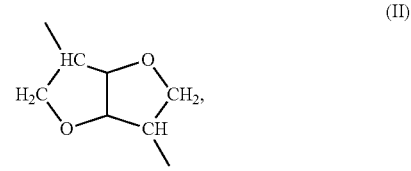

except that for unsaturated polymers having the structural formula (I), $R_1$ and $R_4$ are selected from $(C_2$-$C_{20})$alkylene and $(C_2$-$C_{20})$alkenylene; wherein at least one of $R_1$ and $R_4$ is ($C_2$-$C_{20}$) alkenylene; n is about 5 to about 150; each $R_2$ is independently selected from hydrogen and ($C_6$-$C_{10}$)aryl($C_1$-$C_6$)alkyl; and each $R_3$ is independently selected from hydrogen, ($C_1$-$C_6$)alkyl, ($C_2$-$C_6$)alkenyl, ($C_2$-$C_6$)alkynyl, and ($C_6$-$C_{10}$)aryl($C_1$-$C_6$)alkyl.

In one alternative, $R_3$ is $CH_2Ph$ and the alpha amino acid used in synthesis is L-phenylalanine.

In alternatives wherein $R_3$ is $CH_2$—$CH(CH_3)_2$, the polymer contains the alpha-amino acid, leucine. By varying $R_3$, other alpha amino acids can also be used, e.g., glycine (when $R_3$ is H), alanine (when $R_3$ is $CH_3$), valine (when $R_3$ is $CH(CH_3)_2$), isoleucine (when $R_3$ is $CH(CH_3)$—$CH_2$—$CH_3$), phenylalanine (when $R_3$ is $CH_2$—$C_6H_5$), or lysine (when $R_3$=$(CH_2)_4$—$NH_2$).

The polymer molecules may also have the active agent attached thereto, optionally via a linker or incorporated into a crosslinker between molecules. For example, in one embodiment, the polymer is contained in a polymer-bioactive agent conjugate having the structural formula (III):

Alternatively still, as shown in structural formula (V) below, a linker, —X—Y—, can be inserted between $R_5$ and bioactive agent $R_6$ in the molecule of structural formula III, wherein X is selected from the group consisting of ($C_1$-$C_{18}$) alkylene, substituted alkylene, ($C_3$-$C_8$) cycloalkylene, substituted cycloalkylene, 5-6 membered heterocyclic system containing 1-3 heteroatoms selected from the group O, N, and S, substituted heterocyclic, ($C_2$-$C_{18}$)alkenyl, substituted alkenyl, alkynyl, substituted alkynyl, $C_6$ and $C_{10}$ aryl, substituted aryl, heteroaryl, substituted heteroaryl, alkylaryl, substituted alkylaryl, arylalkynyl, substituted arylalkynyl, arylalkenyl, substituted arylalkenyl, arylalkynyl, substituted arylkynyl and wherein the substituents are selected from the group H, F, Cl, Br, I, ($C_1$-$C_6$)alkyl, —CN, —$NO_2$, —OH, —O($C_1$-$C_4$) alkyl), —S($C_1$-$C_6$)alkyl), —S[(=O)($C_1$-$C_6$)alkyl)], —S[($O_2$)($C_1$-$C_6$)alkyl], —C[(=O)($C_1$-$C_6$)alkyl], $CF_3$, —O[(CO)—($C_1$-$C_6$)alkyl)], —S($O_2$)[N($R_9R_{10}$), —NH

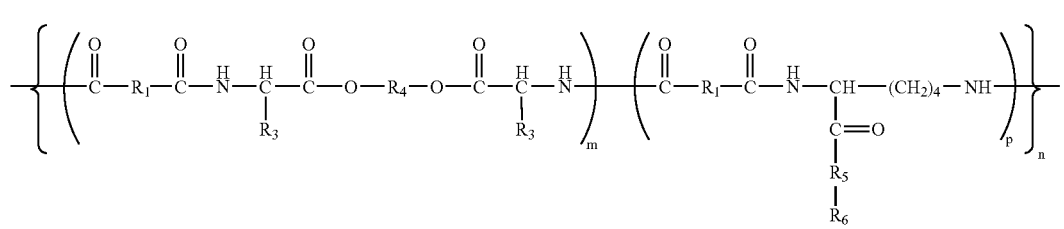

Formula (III)

wherein n, m, p, $R_1$, $R_3$, and $R_4$ are as above, $R_5$ is selected from the group consisting of —O—, —S—, and —$NR_8$—, wherein $R_8$ is H or (C1-C8)alkyl; and $R_6$ is a bioactive agent.

In yet another embodiment, two molecules of the polymer can be crosslinked to provide an —$R_5$—$R_6$—$R_5$— conjugate. In another embodiment, as shown in structural formula IV below, the bioactive agent is covalently linked to one molecule of the polymer through the —$R_5$—$R_6$—$R_5$— conjugate and $R_5$ is independently selected from the group consisting of —O—, —S—, and —$NR_8$—, wherein $R_8$ is H or ($C_1$-$C_8$) alkyl.

[(C=O)($C_1$-$C_6$)alkyl], —NH(C=O)N($R_9R_{10}$), and —N($R_9R_{10}$); where $R_9$ and $R_{10}$ are independently H or ($C_1$-$C_6$)alkyl; and Y is selected from the group consisting of —O—, —S—, —S—S—, —S(O)—, —S($O_2$)—, —$NR_8$—, —C(=O)—, —OC(=O)—, —C(=O)O—, —OC(=O)NH—, —$NR_8$C(=O)—, —C(=O)$NR_8$—, —$NR_8$C(=O)$NR_8$—, —$NR_8$C(=O)$NR_8$—, and —$NR_8$C(=S)$NR_8$—.

Alternatively, one molecule of the polymer is covalently linked to a bioactive agent through an —$R_5$—$R_6$—Y—X—$R_5$— bridge (Formula VI).

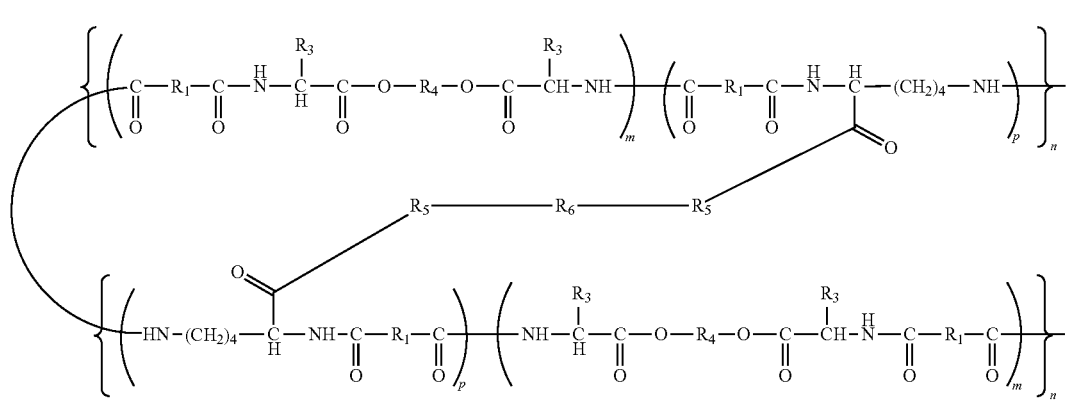

Formula (IV)

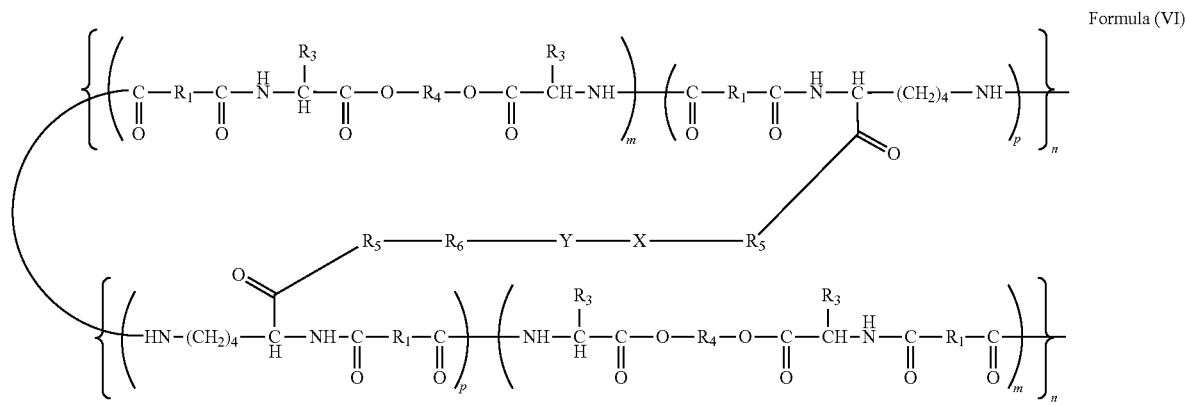

Formula (VI)

wherein, X is selected from the group consisting of ($C_1$-$C_{18}$) alkylene, substituted alkylene, ($C_3$-$C_8$) cycloalkylene, substituted cycloalkylene, 5-6 membered heterocyclic system containing 1-3 heteroatoms selected from the group O, N, and S, substituted heterocyclic, ($C_2$-$C_{18}$)alkenyl 1, substituted alkenyl, alkynyl, substituted alkynyl, $C_6$ and $C_{10}$)aryl, substituted aryl, heteroaryl, substituted heteroaryl, alkylaryl, substituted alkylaryl, arylalkynyl, substituted arylalkynyl, arylalkenyl, substituted arylalkenyl, arylalkynyl, substituted arylkynyl, wherein the substituents are selected from the group consisting of H, F, Cl, Br, I, ($C_1$-$C_6$)alkyl, —CN, —$NO_2$, —OH, —O($C_1$-$C_4$alkyl), —S($C_1$-$C_6$)alkyl), —S[(=O)($C_1$-$C_6$ alkyl)], —S[($O_2$)($C_1$-$C_6$)alkyl], —C[(=O)($C_1$-$C_6$)alkyl], $CF_3$, —O[(CO)—($C_1$-$C_6$)alkyl)], —S($O_2$)[N($R_9R_{10}$), —NH[(C=O)($C_1$-$C_6$)alkyl], —NH(C=O)N($R_9R_{10}$), and —N($R_{11}R_{12}$), wherein $R_1$ is independently ($C_2$-$C_{20}$)alkylene and ($C_2$-$C_{20}$)alkenylene, and $R_{11}$, $R_{12}$ are independently H or ($C_1$-$C_6$)alkyl.

In another embodiment, the polymer coating on the invention stents and medical devices comprises four partially crosslinked molecules of the polymer of structural formula (III), except that only two of the four molecules omit $R_6$ and are crosslinked to provide a single —$R_5$—X—$R_5$— conjugate, wherein X is selected from the group consisting of ($C_1$-$C_{18}$) alkylene, substituted alkylene, ($C_3$-$C_8$) cycloalkylene, substituted cycloalkylene, 5-6 membered heterocyclic system containing 1-3 heteroatoms selected from the group consisting of O, N, and S, substituted heterocyclic, ($C_2$-$C_{18}$) alkenyl, substituted alkenyl, alkynyl, substituted alkynyl, $C_6$ and $C_{10}$ aryl, substituted aryl, heteroaryl, substituted heteroaryl, alkylaryl, substituted alkylaryl, arylalkynyl, substituted arylalkynyl, arylalkenyl, substituted arylalkenyl, arylalkynyl, and substituted arylkynyl and wherein the substituents are selected from the group consisting of H, F, Cl, Br, I, ($C_1$-$C_6$)alkyl, —CN, —$NO_2$, —OH, —O($C_1$-$C_4$)alkyl), —S($C_1$-$C_6$)alkyl), —S[(=O)($C_1$-$C_6$)alkyl)], —S[($O_2$)($C_1$-$C_6$)alkyl], —C[(=O)($C_1$-$C_6$)alkyl], $CF_3$, —O[(CO)—($C_1$-$C_6$)alkyl)], —S($O_2$)[N($R_9R_{10}$), —NH[(C=O)($C_1$-$C_6$)alkyl], —NH(C=O)N($R_9R_{10}$), and —N($R_9R_{10}$); wherein $R_9$ and $R_{10}$ are independently H or ($C_1$-$C_6$) alkyl).

In yet another embodiment, four molecules of the polymer of structural formula III can be partially crosslinked by omitting $R_6$ on two of the molecules and forming instead a single —$R_5$—X—$R_7$— conjugate, wherein X, $R_5$, $R_6$ and $R_7$ are as described above and as shown in structural formula (VII), wherein q+s=n:

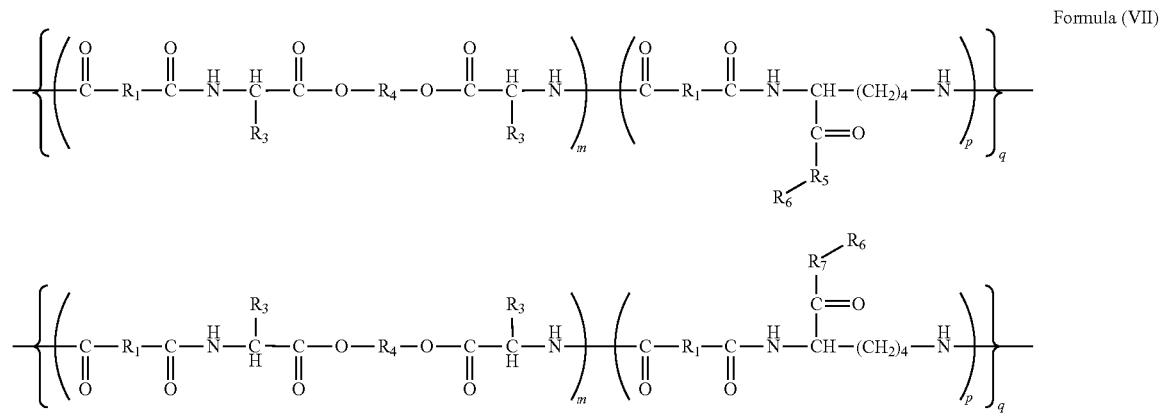

Formula (VII)

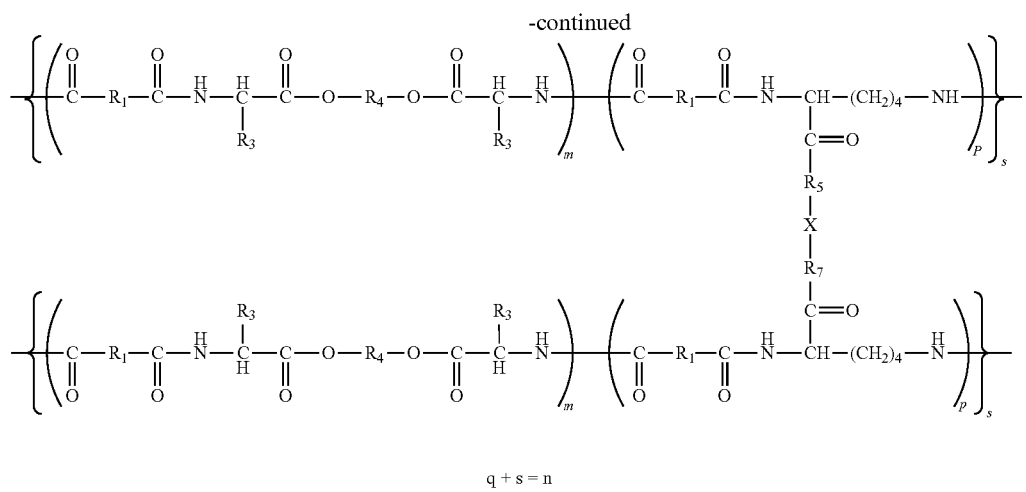

$q + s = n$

The term "aryl" is used with reference to structural formulae herein to denote a phenyl radical or an ortho-fused bicyclic carbocyclic radical having about nine to ten ring atoms in which at least one ring is aromatic. In certain embodiments, one or more of the ring atoms can be substituted with one or more of nitro, cyano, halo, trifluoromethyl, or trifluoromethoxy. Examples of aryl include, but are not limited to, phenyl, naphthyl, and nitrophenyl.

The term "alkenylene" is used with reference to structural formulae herein to mean a divalent branched or unbranched hydrocarbon chain containing at least one unsaturated bond in the main chain or in a side chain.

The molecular weights and polydisperities herein are determined by gel permeation chromatograph using polystyrene standards. More particularly, number and weight average molecular weights ($M_n$ and $M_w$) are determined, for example, using a Model 510 gel permeation chromatograph (Water Associates, Inc., Milford, Mass.) equipped with a high-pressure liquid chromatographic pump, a Waters 486 UV detector and a Waters 2410 differential refractive index detector. Tetrahydrofuran (THF) is used as the eluent (1.0 mL/min). The polystyrene standards have a narrow molecular weight distribution.

Methods for making the polymers of structural formula (I-VII), containing a α-amino acid in the general formula are well known in the art. For example, for the embodiment of the polymer of structural formula (I) wherein R is incorporated into an α-amino acid, for polymer synthesis the α-amino acid can be converted into a bis-α-amino acid, for example, by condensing the α-amino acid with a diol HO—$R^2$—OH. As a result, ester fragments are formed. Then, the bis-α-amino acid is entered into a polycondensation reaction with a di-acid such as sebacic acid, to obtain the final polymer having both ester and amide bonds. Alternatively, instead of the di-acid, a di-acid derivative such as activated di-ester, e.g., di-para-nitrophenoxy. di-acid chloride can also be used.

More particularly, synthesis of the unsaturated poly(ester-amide)s (UPEAs) useful as biodegradable polymers of the structural formula (I) as described above will be described wherein

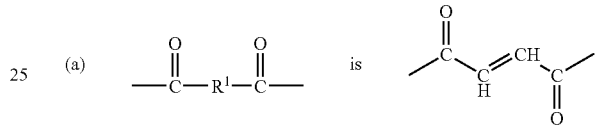

and/or (b) $R^4$ is —$CH_2$—CH=CH—$CH_2$—. In cases where (a) is present and (b) is not present, $R^4$ in (I) is —$C_4H_8$— or —$C_6H_{12}$—. In cases where (a) is not present and (b) is present, $R^1$ in (I) is —$C_4H_8$— or —$C_8H_{16}$—.

The unsaturated PEAs can be prepared by solution polycondensation of either (1) di-p-toluene sulfonic acid salt of diester of alpha-amino acid and unsaturated diol and di-p-nitrophenyl ester of saturated dicarboxylic acid or (2) di-p-toluene sulfonic acid salt of alpha-amino acid and saturated diol and di-nitrophenyl ester of unsaturated dicarboxylic acid or (3) di-p-toluene sulfonic acid salt of diester of alpha-amino acid and unsaturated diol and di-nitrophenyl ester of unsaturated dicarboxylic acid.

The aryl sulfonic acid salts are used instead of the free amine base because the aryl sulfonic acid group is a very good leaving group which can promote the condensation reaction to move to the right of the reaction equation so product is obtained in high yield and because the p-toluene sulfonic acid salts are known for use in synthesizing polymers containing amino acid residues.

The di-p-nitrophenyl esters of unsaturated dicarboxylic acid can be synthesized from p-nitrophenyl and unsaturated dicarboxylic acid chloride, e.g., by dissolving triethylamine and p-nitrophenyl in acetone and adding unsaturated dicarboxylic acid chloride drop wise with stirring at −78° C. and pouring into water to precipitate product. Suitable acid chlorides included acrylic methacrylic, crotonic, isocrotonic, angelic, tiglic, sorbic, cinnamic, allocinnamic, phenylpropiolic, fumaric, maleic, mesaconic, citraconic, glutaconic, itaconic, ethenyl-butane dioic and 2-propenyl-butanedioic acid chlorides. Additional compounds that can be used in the place of di-p-nitrophenyl esters of unsaturated dicarboxylic acid include those having structural formula (VIII):

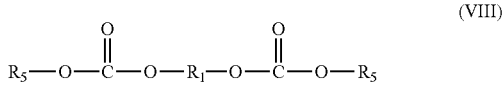

wherein each $R_5$ is independently $(C_1-C_{10})$aryl optionally substituted with one or more nitro, cyano, halo, trifluoromethyl, or trifluoromethoxy; and $R_1$ is independently $(C_2-C_{20})$ alkylene or $(C_2-C_8)$alkyloxy$(C_2-C_{20})$alkylene.

The di-aryl sulfonic acid salts of diesters of alpha-amino acid and unsaturated diol can be prepared by admixing alpha-amino acid, e.g., p-aryl sulfonic acid monohydrate and saturated or unsaturated diol in toluene, heating to reflux temperature, until water evolution is minimal, then cooling. The unsaturated diols include, for example, 2-butene-1,3-diol and 1,18-octadec-9-en-diol.

Saturated di-p-nitrophenyl esters of dicarboxylic acid and saturated di-p-toluene sulfonic acid salts of bis-alpha-amino acid esters can be prepared as described in U.S. Pat. No. 6,503,538 B1.

Synthesis the unsaturated poly(ester-amide)s (UPEAs) useful as biodegradable polymers of the structural formula (II) as described above will now be described. Compounds having the structural formula (II) can be made in similar fashion to the compound (VII) of U.S. Pat. No. 6,503,538 B1, except that $R^4$ of (III) of U.S. Pat. No. 6,503,535 and/or $R^1$ of (V) of U.S. Pat. No. 6,503,538 is $C_2-C_{20}$ alkenylene as described above. The reaction is carried out, for example, by adding dry triethylamine to a mixture of said (III) and (IV) of U.S. Pat. No. 6,503,538 and said (V) in dry N,N-dimethylacetamide, at room temperature, then increasing the temperature to 80° C. and stirring for 16 hours, then cooling the reaction solution to room temperature, diluting with ethanol, pouring into water, separating polymer, washing separated polymer with water, drying to about 30° C. under reduced pressure and then purifying up to negative test on p-nitrophenyl and p-toluene sulfonic acid. A preferred reactant (IV) is p-toluene sulfonic acid salt of benzyl ester, the benzyl ester protecting group is preferably removed from (II) to confer biodegradability, but it should not be removed by hydrogenolysis as in Example 22 of U.S. Pat. No. 6,503,538 because hydrogenolysis would saturate the desired double bonds; rather the benzyl ester group should be converted to an acid group by a method that would preserve unsaturation, e.g., by treatment with fluoroacetic acid or gaseous HF. Alternatively, the lysine reactant (IV) can be protected by a protecting group different from benzyl which can be readily removed in the finished product while preserving unsaturation, e.g., the lysine reactant can be protected with t-butyl (i.e., the reactant can be t-butyl ester of lysine) and the t-butyl can be converted to H while preserving unsaturation by treatment of the product (II) with dilute acid.

A working example of the compound having structural formula (II) is provided by substituting p-toluene sulfonic acid salt of L-phenylalanine 2-butene-1,4-diester for (III) in Example 1 of U.S. Pat. No. 6,503,538 or by substituting di-p-nitrophenyl fumarate for (V) in Example 1 of U.S. Pat. No. 6,503,538 or by substituting p-toluene sulfonic acid salt of L-phenylalanine 2-butene-1,3-diester for III in Example 1 of U.S. Pat. No. 6,503,538 and also substituting de-p-nitrophenyl fumarate for (V) in Example 1 of U.S. Pat. No. 6,503, 538.

In unsaturated compounds having either structural formula (I-VII), the following hold: Aminoxyl radical (e.g., 4-amino TEMPO) can be attached using carbonyldiimidazol as a condensing agent. Bioactive agents, as described herein, can be attached via the double bond functionality. Hydrophilicity can be imparted by bonding to poly(ethylene glycol) diacrylate.

In yet another aspect, polymers contemplated for use in forming the invention polymer coated stents and medical devices include those set forth in U.S. Pat. Nos. 5,516,881; 6,338,047; 6,476,204; 6,503,538; and in U.S. application Ser. Nos. 10/096,435; 10/101,408; 10/143,572; and 10/194,965; the entire contents of each of which is incorporated herein by reference.

The PEA/PEUR polymers described herein may contain up to two amino acids per monomer and preferably have weight average molecular weights ranging from 10,000 to 125,000; these polymers and copolymers typically have inherent viscosities at 25° C., determined by standard viscosimetric methods, ranging from 0.3 to 4.0, preferably ranging from 0.5 to 3.5.

Polymers contemplated for use in the practice of the invention can be synthesized by a variety of methods well known in the art. For example, tributyltin (IV) catalysts are commonly used to form polyesters such as poly(caprolactone), poly(glycolide), poly(lactide), and the like. However, it is understood that a wide variety of catalysts can be used to form polymers suitable for use in the practice of the invention.

Such poly(caprolactones) contemplated for use have an exemplary structural formula (IX) as follows:

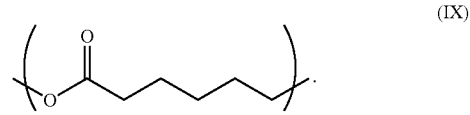

Poly(glycolides) contemplated for use have an exemplary structural formula (X) as follows:

Poly(lactides) contemplated for use have an exemplary structural formula (XI) as follows:

An exemplary synthesis of a suitable poly(lactide-co-ε-caprolactone) including an aminoxyl moiety is set forth as follows. The first step involves the copolymerization of lactide and ε-caprolactone in the presence of benzyl alcohol using stannous octoate as the catalyst to form a polymer of structural formula (XII).

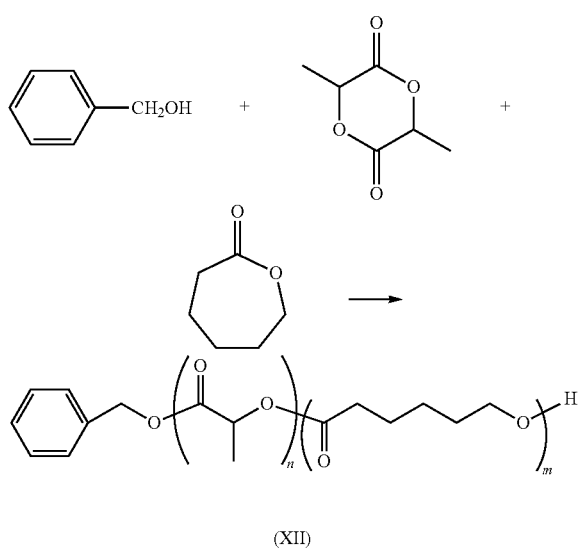

(XII)

The hydroxy terminated polymer chains can then be capped with maleic anhydride to form polymer chains having structural formula (XIII):

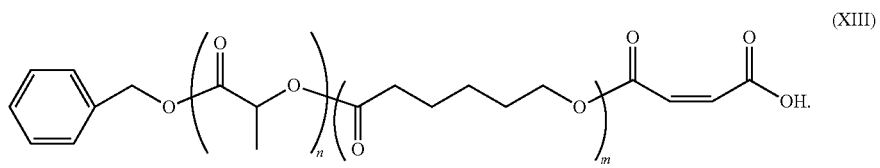

At this point, 4-amino-2,2,6,6-tetramethylpiperidine-1-oxy can be reacted with the carboxylic end group to covalently attach the aminoxyl moiety to the copolymer via the amide bond that results from the reaction between the 4-amino group and the carboxylic acid end group. Alternatively, the maleic acid capped copolymer can be grafted with polyacrylic acid to provide additional carboxylic acid moieties for subsequent attachment of further aminoxyl groups.

The PEA/PEUR polymers described herein can be fabricated in a variety of molecular weights, and the appropriate molecular weight for use with a given bioactive agent is readily determined by one of skill in the art. Thus, e.g., a suitable molecular weight will be on the order of about 5,000 to about 300,000, for example about 5,000 to about 250,000, or about 75,000 to about 200,000, or about 100,000 to about 150,000.

Polymers useful in the making the invention polymer coated stents and medical devices, such as PEA/PEUR polymers, biodegrade by enzymatic action at the surface. Therefore, the polymers administer the bioactive agent to the subject at a controlled release rate, which is specific and constant over a prolonged period. Additionally, since PEA/PEUR polymers break down in vivo via hydrolytic enzymes without production of adverse side products, the polymer coatings on the invention stents and medical devices are substantially non-inflammatory.

As used herein "dispersed" means at least one bioactive agent as disclosed herein is dispersed, mixed, dissolved, homogenized, and/or covalently bound ("dispersed") in a polymer, for example attached to the surface of the polymer or polymer coating.

While the bioactive agents can be dispersed within the polymer matrix without chemical linkage to the polymer carrier, it is also contemplated that the bioactive agent or additional bioactive agent can be covalently bound to the biodegradable polymers via a wide variety of suitable functional groups. For example, when the biodegradable polymer is a polyester, the carboxyl group chain end can be used to react with a complimentary moiety on the bioactive agent or additional bioactive agent, such as hydroxy, amino, thio, and the like. A wide variety of suitable reagents and reaction conditions are disclosed, e.g., in *Advanced Organic Chemistry, Reactions, Mechanisms, and Structure*, Fifth Edition, (2001); and *Comprehensive Organic Transformations*, Second Edition, Larock (1999).

In other embodiments, a bioactive agent can be linked to any of the polymers of structures (I)-(VII) through an amide, ester, ether, amino, ketone, thioether, sulfinyl, sulfonyl, or disulfide linkage. Such a linkage can be formed from suitably functionalized starting materials using synthetic procedures that are known in the art.

For example, in one embodiment a polymer can be linked to the bioactive agent or additional bioactive agent via a carboxyl group (e.g., COOH) of the polymer. Specifically, a compound of structures (I) and (III) can react with an amino functional group or a hydroxyl functional group of a bioactive agent to provide a biodegradable polymer having the bioactive agent attached via an amide linkage or carboxylic ester linkage, respectively. In another embodiment, the carboxyl group of the polymer can be benzylated or transformed into an acyl halide, acyl anhydride/"mixed" anhydride, or active ester. In other embodiments, the free —$NH_2$ ends of the polymer molecule can be acylated to assure that the bioactive agent will attach only via a carboxyl group of the polymer and not to the free ends of the polymer.

Alternatively, the bioactive agent or additional bioactive agent can be attached to the polymer via a linker molecule, for example, as described in structural formulae (V-VII). Indeed, to improve surface hydrophobicity of the biodegradable polymer, to improve accessibility of the biodegradable polymer towards enzyme activation, and to improve the release profile of the biodegradable polymer, a linker may be utilized to indirectly attach the bioactive agent and/or adjuvant to the biodegradable polymer. In certain embodiments, the linker compounds include poly(ethylene glycol) having a molecular weight (MW) of about 44 to about 10,000, preferably 44 to 2000; amino acids, such as serine; polypeptides with repeat number from 1 to 100; and any other suitable low molecular weight polymers. The linker typically separates the bioactive agent from the polymer by about 5 angstroms up to about 200 angstroms.

In still further embodiments, the linker is a divalent radical of formula W-A-Q, wherein A is ($C_1$-$C_{24}$)alkyl, ($C_2$-$C_{24}$) alkenyl, ($C_2$-$C_{24}$)alkynyl, ($C_3$-$C_8$)cycloalkyl, or ($C_6$-$C_{10}$) aryl, and W and Q are each independently —N(R)C(=O)—, —C(=O)N(R)—, —OC(=O)—, —C(=O)O—, —O—, —S—, —S(O), —S(O)$_2$—, —S—S—, —N(R)—, —C(=O)—, wherein each R is independently H or (C$_1$-C$_6$) alkyl.

As used to describe the above linkers, the term "alkyl" refers to a straight or branched chain hydrocarbon group including methyl, ethyl, n-propyl, isopropyl, n-butyl, isobutyl, tert-butyl, n-hexyl, and the like.

As used herein, "alkenyl" refers to straight or branched chain hydrocarbyl groups having one or more carbon-carbon double bonds.

As used herein, "alkynyl" refers to straight or branched chain hydrocarbyl groups having at least one carbon-carbon triple bond.

As used herein, "aryl" refers to aromatic groups having in the range of 6 up to 14 carbon atoms.

In certain embodiments, the linker may be a polypeptide having from about 2 up to about 25 amino acids. Suitable peptides contemplated for use include poly-L-glycine, poly-L-lysine, poly-L-glutamic acid, poly-L-aspartic acid, poly-L-histidine, poly-L-ormithine, poly-L-serine, poly-L-threonine, poly-L-tyrosine, poly-L-leucine, poly-L-lysine-L-phenylalanine, poly-L-arginine, poly-L-lysine-L-tyrosine, and the like.

In one embodiment, the bioactive agent can covalently crosslink the polymer, i.e. the bioactive agent is bound to more than one polymer molecule. This covalent crosslinking can be done with or without additional polymer-bioactive agent linker.

The bioactive agent molecule can also be incorporated into an intramolecular bridge by covalent attachment between two polymer molecules.

A linear polymer polypeptide conjugate is made by protecting the potential nucleophiles on the polypeptide backbone and leaving only one reactive group to be bound to the polymer or polymer linker construct. Deprotection is performed according to methods well known in the art for deprotection of peptides (Boc and Fmoc chemistry for example).

In one embodiment of the present invention, a polypeptide bioactive agent is presented as retro-inverso or partial retro-inverso peptide. Accordingly, the terms "peptide" and "polypeptide," as used herein, include peptides, wholly peptide derivatives (such as branched peptides) and covalent hetero- (such as glyco- and lipo- and glycolipo-) derivatives of peptides.

The peptides described herein can be synthesized using any technique as is known in the art. The peptides and polypeptides can also include "peptide mimetics." Peptide analogs are commonly used in the pharmaceutical industry as non-peptide bioactive agents with properties analogous to those of the template peptide. These types of non-peptide compound are termed "peptide mimetics" or "peptidomimetics." Fauchere, J. (1986) *Adv. Bioactive agent Res.*, 15:29; VeberandFreidinger (1985) TINS p. 392; and Evans et al. (1987) *J. Med. Chem.*, 30:1229; and are usually developed with the aid of computerized molecular modeling. Generally, peptidomimetics are structurally similar to a paradigm polypeptide (i.e., a polypeptide that has a biochemical property or pharmacological activity), but have one or more peptide linkages optionally replaced by a linkage selected from the group consisting of: —CH$_2$NH—, —CH$_2$S—, CH$_2$—CH$_2$—, —CH=CH— (cis and trans), —COCH$_2$—, —CH(OH)CH$_2$—, and —CH$_2$SO—, by methods known in the art and further described in the following references: Spatola, A. F. in "Chemistry and Biochemistry of Amino Acids, Peptides, and Proteins," B. Weinstein, eds., Marcel Dekker, New York, p. 267 (1983); Spatola, A. F., *Vega Data* (March 1983), Vol. 1, Issue 3, "Peptide Backbone Modifications" (general review); Morley, J. S., *Trends. Pharm. Sci.*, (1980) pp. 463-468 (general review); Hudson, D. et al., *Int. J. Pept. Prot. Res.*, (1979) 14:177-185 (—CH$_2$NH—, CH$_2$CH$_2$—); Spatola, A. F. et al., *Life Sci.*, (1986) 38:1243-1249 (—CH$_2$—S—); Harm, M. M., *J. Chem. Soc. Perkin Trans I* (1982) 307-314 (—CH=CH—, cis and trans); Almquist, R. G. et al., *J. Med. Chem.*, (1980) 23:2533 (—COCH$_2$—); Jennings-Whie, C. et al., *Tetrahedron Lett.*, (1982) 23:2533 (—COCH$_2$—); Szelke, M. et al., *European Appln.*, EP 45665 (1982) CA: 97:39405 (1982) (—CH(OH)CH$_2$—); Holladay, M. W. et al., *Tetrahedron Lett.*, (1983) 24:4401-4404 (—C(OH)CH$_2$—); and Hruby, V. J., *Life Sci.*, (1982) 31:189-199 (—CH$_2$—S—). Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others.

Additionally, substitution of one or more amino acids within a peptide or polypeptide (e.g., with a D-Lysine in place of L-Lysine) may be used to generate more stable peptides and peptides resistant to endogenous proteases. Alternatively, the synthetic peptide or polypeptide, e.g., covalently bound to the biodegradable polymer, can also be prepared from D-amino acids, referred to as inverso peptides. When a peptide is assembled in the opposite direction of the native peptide sequence, it is referred to as a retro peptide. In general, peptides prepared from D-amino acids are very stable to enzymatic hydrolysis. Many cases have been reported of preserved biological activities for retro-inverso or partial retro-inverso peptides (U.S. Pat. No. 6,261,569 B1 and references therein; B. Fromme et al, Endocrinology (2003) 144:3262-3269).

The linker can be attached first to the polymer or to the bioactive agent or additional bioactive agent. During synthesis, the linker can be either in unprotected form or protected form, using a variety of protecting groups well known to those skilled in the art. In the case of a protected linker, the unprotected end of the linker can first be attached to the polymer or the bioactive agent or additional bioactive agent. The protecting group can then be de-protected using Pd/H$_2$ hydrogenation, mild acid or base hydrolysis, or any other common de-protection method that is known in the art. The de-protected linker can then be attached to the bioactive agent or additional bioactive agent, or to the polymer An exemplary synthesis of a biodegradable polymer according to the invention (wherein the molecule to be attached is an aminoxyl) is set forth as follows. A polyester can be reacted with an aminoxyl, e.g., 4-amino-2,2,6,6-tetramethylpiperidine-1-oxy, in the presence of N,N'-carbonyl diimidazole to replace the hydroxyl moiety in the carboxyl group at the chain end of the polyester with imino linked to aminoxyl-containing radical, so that the imino moiety covalently bonds to the carbon of the carbonyl residue of the carboxyl group. The N,N'-carbonyl diimidazole converts the hydroxyl moiety in the carboxyl group at the chain end of the polyester into an intermediate product moiety which will react with the aminoxyl, e.g., 4-amino-2,2,6,6-tetramethylpiperidine-1-oxy. The aminoxyl reactant is typically used in a mole ratio of reactant to polyester ranging from 1:1 to 100:1. The mole ratio of N,N'-carbonyl diimidazole to aminoxyl is preferably about 1:1.

A typical reaction is as follows. A polyester is dissolved in a reaction solvent and reaction is readily carried out at the temperature utilized for the dissolving. The reaction solvent may be any in which the polyester will dissolve; this information is normally available from the manufacturer of the polyester. When the polyester is a polyglycolic acid or a poly(glycolide-L-lactide) (having a monomer mole ratio of glycolic acid to L-lactic acid greater than 50:50), highly refined (99.9+% pure) dimethyl sulfoxide at 115° C. to 130° C. or DMSO at room temperature suitably dissolves the polyester. When the polyester is a poly-L-lactic acid, a poly-DL-lactic acid or a poly(glycolide-L-lactide) (having a monomer mole ratio of glycolic acid to L-lactic acid 50:50 or less than 50:50), tetrahydrofuran, dichloromethane (DCM) and chloroform at room temperature to 40~50° C. suitably dissolve the polyester.

Polymer—Bioactive Agent Linkage

In one embodiment, the polymers used to make the surface covering for the invention stents and other medical devices as described herein have one or more bioactive agent directly linked to the polymer. The residues of the polymer can be linked to the residues of the one or more bioactive agents. For example, one residue of the polymer can be directly linked to one residue of the bioactive agent. The polymer and the bioactive agent can each have one open valence.

Alternatively, more than one bioactive agent, multiple bioactive agents, or a mixture of bioactive agents and additional bioactive agents having different therapeutic or palliative activity can be directly linked to the polymer. However, since the residue of each bioactive agent can be linked to a corresponding residue of the polymer, the number of residues of the one or more bioactive agents can correspond to the number of open valences on the residue of the polymer.

As used herein, a "residue of a polymer" refers to a radical of a polymer having one or more open valences. Any synthetically feasible atom, atoms, or functional group of the polymer (e.g., on the polymer backbone or pendant group) of the present invention can be removed to provide the open valence, provided bioactivity is substantially retained when the radical is attached to a residue of a bioactive agent. Additionally, any synthetically feasible functional group (e.g., carboxyl) can be created on the polymer (e.g., on the polymer backbone or pendant group) to provide the open valence, provided bioactivity is substantially retained when the radical is attached to a residue of a bioactive agent. Based on the linkage that is desired, those skilled in the art can select suitably functionalized starting materials that can be derived from the polymer of the present invention using procedures that are known in the art.

As used herein, a "residue of a compound of structural formula (*)" refers to a radical of a compound of polymer formulas (I-VII) as described herein having one or more open valences. Any synthetically feasible atom, atoms, or functional group of the compound (e.g., on the polymer backbone or pendant group) can be removed to provide the open valence, provided bioactivity is substantially retained when the radical is attached to a residue of a bioactive agent. Additionally, any synthetically feasible functional group (e.g., carboxyl) can be created on the compound of formulas (I-VII) (e.g., on the polymer backbone or pendant group) to provide the open valance, provided bioactivity is substantially retained when the radical is attached to a residue of a bioactive agent. Based on the linkage that is desired, those skilled in the art can select suitably functionalized starting materials that can be derived from the compound of formulas (I-VII) using procedures that are known in the art.

For example, the residue of a bioactive agent can be linked to the residue of a compound of structural formula (I-VII) through an amide (e.g., —N(R)C(=O)— or —C(=O)N (R)—), ester (e.g., —OC(=O)— or —C(=O)O—), ether (e.g., —O—), amino (e.g., —N(R)—), ketone (e.g., —C(=O)—), thioether (e.g., —S—), sulfinyl (e.g., —S(O)—), sulfonyl (e.g., —S(O)$_2$—), disulfide (e.g., —S—S—), or a direct (e.g., C—C bond) linkage, wherein each R is independently H or ($C_1$-$C_6$)alkyl. Such a linkage can be formed from suitably functionalized starting materials using synthetic procedures that are known in the art. Based on the linkage that is desired, those skilled in the art can select suitably functional starting material that can be derived from a residue of a compound of structural formula (I-VII) and from a given residue of a bioactive agent or adjuvant using procedures that are known in the art. The residue of the bioactive agent or adjuvant can be linked to any synthetically feasible position on the residue of a compound of structural formula (I-VII). Additionally, the invention also provides compounds having more than one residue of a bioactive agent or adjuvant bioactive agent directly linked to a compound of structural formula (I-VII).

The number of bioactive agents that can be linked to the polymer molecule can typically depend upon the molecular weight of the polymer. For example, for a compound of structural formula (I), wherein n is about 5 to about 150, preferably about 5 to about 70, up to about 150 bioactive agent molecules (i.e., residues thereof) can be directly linked to the polymer (i.e., residue thereof) by reacting the bioactive agent with side groups of the polymer. In unsaturated polymers, the bioactive agents can also be reacted with double (or triple) bonds in the polymer.

Stents according to the invention are typically cylindrical in shape. The walls of the stent structure can be formed of metal or polymer with openings therein, e.g., a mesh. The stent is implanted into a body lumen, such as a blood vessel, where it stays permanently or biodegrades, to keep the vessel open and to improve blood flow to the heart muscle and promote natural wound healing processes at a location of damaged endothelium. Stents can also be positioned in vasculature in other parts of the body, such as the kidneys or the brain. The stenting procedure is fairly common, and various types of stents have been developed and used as is known in the art.

The polymers described herein can be coated onto the surface of a porous stent structure or other medical device as described here in many ways, such as dip-coating, spray-coating, ionic deposition, and the like, as is well known in the art. In coating a porous stent, care must be taken not to occlude the pores in the stent structure, which are needed to allow access and migration from the interior of the vessel to the vessel wall of blood borne progenitor endothelial cells and other blood factors that participate in the natural biological process of wound healing.

Alternatively, the polymer coating on the surface of the stent structure can be a formed as a polymer sheath that is applied over the stent structure. In this embodiment the sheath serves as a partial physical barrier to macrophages so that a relatively small number of smooth muscle cells are activated to cause neointimal proliferation. To allow for sufficient movement of bioactive material across the porous stent structure, such as progenitor endothelial cells from the blood stream, the sheath can be laser ablated to form openings in the polymer coating. The stent structure can be moved while the laser is held stationary to ablate the structure into a pattern, or alternatively, the laser can be programmed to move along a predetermined pattern by a method known to artisans. A combination of both, i.e. moving both the laser and the structure, is also possible. In the present invention, even a coated stent having a complex stent pattern can be made with high precision.

The stent structure can be formed of any suitable substance, such as is known in the art, that can be processed (e.g., molded, stamped, woven, etc.) to contain the porous surface features described herein. For example, the stent body can be formed from a biocompatible metal, such as stainless steel, tantalum, nitinol, elgiloy, and the like, as well as suitable combinations thereof.

For example, metal stent structures can be formed of a material comprising metallic fibers uniformly laid to form a three-dimensional non-woven matrix and sintered to form a labyrinth structure exhibiting high porosity, typically in a range from about 50 percent to about 85 percent, preferably at least about 70 percent. The metal fibers typically have a diameter in the range from about 1 micron to 25 microns. Pores in the stent structure can have an average diameter in the range from about 30 microns to about 65 microns. For use in coronary arteries, the stent structure should be made of 100% stainless steel, with fully annealed stainless steel being a preferred metal. The stent structure can be of the type that is balloon expandable, as is known in the art.

In one embodiment, the stent structure is itself entirely biodegradable, being made of cross-linkable "star structure polymers", or dendrimers, which are well known to those skilled in the art. In one aspect, the stent structure is formed from biodegradable cross-linked poly(ester amide), polycaprolactone, or poly(ester urethane) as described herein. In invention multilayered biodegradable stents, the stent structure (i.e., the "stent struts") is preferably biodegradable and hence are made of such cross-linkable polymers or dendrimers.

Residues of the polymers described herein can be formed employing any suitable reagents and reaction conditions. Suitable reagents and reaction conditions are disclosed, e.g., in *Advanced Organic Chemistry, Part B: Reactions and Synthesis*, Second Edition, Carey and Sundberg (1983); *Advanced Organic Chemistry, Reactions, Mechanisms, and Structure*, Second Edition, March (1977); and *Comprehensive Organic Transformations*, Second Edition, Larock (1999).

Additional bioactive agents As used herein, an "additional bioactive agent" refers to a therapeutic or diagnostic agent other than the "bioactive" agents described above that promote the natural wound healing process of re-endothelialization of vessels as disclosed herein. Such additional bioactive agents can also be attached polymer coatings on the surface of the invention stents or to polymers used for coating other types of insertable or implantable medical or therapeutic devices having different treatment aims as are known in the art, wherein contact of the polymer coating with a treatment surface or blood borne cell or factor or release from the polymer coating by biodegradation is desirable. However, such additional bioactive agents are not used in the inner layer of the invention multilayered stents, which contain only the bioactive agents that promote the natural would healing process of re-endothelialization of vessels.

Specifically, such additional bioactive agent can include, but is not limited to, one or more: polynucleotides, polypeptides, oligonucleotides, gene therapy agents, nucleotide analogs, nucleoside analogs, polynucleic acid decoys, therapeutic antibodies, abciximab, anti-inflammatory agents, blood modifiers, anti-platelet agents, anti-coagulation agents, immune suppressive agents, anti-neoplastic agents, anti-cancer agents, anti-cell proliferation agents, and nitric oxide releasing agents.

The polynucleotide can include deoxyribonucleic acid (DNA), ribonucleic acid (RNA), double stranded DNA, double stranded RNA, duplex DNA/RNA, antisense polynucleotides, functional RNA or a combination thereof. In one embodiment, the polynucleotide can be RNA. In another embodiment, the polynucleotide can be DNA. In another embodiment, the polynucleotide can be an antisense polynucleotide. In another embodiment the polynucleotide can be a sense polynucleotide. In another embodiment, the polynucleotide can include at least one nucleotide analog. In another embodiment, the polynucleotide can include a phosphodiester linked 3'-5' and 5'-3' polynucleotide backbone. Alternatively, the polynucleotide can include non-phosphodiester linkages, such as phosphotioate type, phosphoramidate and peptide-nucleotide backbones. In another embodiment, moieties can be linked to the backbone sugars of the polynucleotide. Methods of creating such linkages are well known to those of skill in the art.

The polynucleotide can be a single-stranded polynucleotide or a double-stranded polynucleotide. The polynucleotide can have any suitable length. Specifically, the polynucleotide can be about 2 to about 5,000 nucleotides in length, inclusive; about 2 to about 1000 nucleotides in length, inclusive; about 2 to about 100 nucleotides in length, inclusive; or about 2 to about 10 nucleotides in length, inclusive.

An antisense polynucleotide is typically a polynucleotide that is complimentary to an mRNA, which encodes a target protein. For example, the mRNA can encode a cancer promoting protein i.e., the product of an oncogene. The antisense polynucleotide is complimentary to the single-stranded mRNA and will form a duplex and thereby inhibit expression of the target gene, i.e., will inhibit expression of the oncogene. The antisense polynucleotides of the invention can form a duplex with the mRNA encoding a target protein and will disallow expression of the target protein.

A "functional RNA" refers to a ribozyme or other RNA that is not translated.

A "polynucleic acid decoy" is a polynucleic acid that inhibits the activity of a cellular factor upon binding of the cellular factor to the polynucleic acid decoy. The polynucleic acid decoy contains the binding site for the cellular factor. Examples of cellular factors include, but are not limited to, transcription factors, polymerases and ribosomes. An example of a polynucleic acid decoy for use as a transcription factor decoy will be a double-stranded polynucleic acid containing the binding site for the transcription factor. Alternatively, the polynucleic acid decoy for a transcription factor can be a single-stranded nucleic acid that hybridizes to itself to form a snap-back duplex containing the binding site for the target transcription factor. An example of a transcription factor decoy is the E2F decoy. E2F plays a role in transcription of genes that are involved with cell-cycle regulation and that cause cells to proliferate. Controlling E2F allows regulation of cellular proliferation. For example, after injury (e.g., angioplasty, surgery, stenting) smooth muscle cells proliferate in response to the injury. Proliferation may cause restenosis of the treated area (closure of an artery through cellular proliferation). Therefore, modulation of E2F activity allows control of cell proliferation and can be used to decrease proliferation and avoid closure of an artery. Examples of other such polynucleic acid decoys and target proteins include, but are not limited to, promoter sequences for inhibiting polymerases and ribosome binding sequences for inhibiting ribosomes. It is understood that the invention includes polynucleic acid decoys constructed to inhibit any target cellular factor.

A "gene therapy agent" refers to an agent that causes expression of a gene product in a target cell through introduction of a gene into the target cell followed by expression. An example of such a gene therapy agent would be a genetic construct that causes expression of a protein, such as insulin, when introduced into a cell. Alternatively, a gene therapy agent can decrease expression of a gene in a target cell. An example of such a gene therapy agent would be the introduction of a polynucleic acid segment into a cell that would integrate into a target gene and disrupt expression of the gene. Examples of such agents include viruses and polynucleotides that are able to disrupt a gene through homologous recombination. Methods of introducing and disrupting genes with cells are well known to those of skill in the art.

An oligonucleotide of the invention can have any suitable length. Specifically, the oligonucleotide can be about 2 to about 100 nucleotides in length, inclusive; up to about 20 nucleotides in length, inclusive; or about 15 to about 30 nucleotides in length, inclusive. The oligonucleotide can be single-stranded or double-stranded. In one embodiment, the oligonucleotide can be single-stranded. The oligonucleotide can be DNA or RNA. In one embodiment, the oligonucleotide can be DNA. In one embodiment, the oligonucleotide can be synthesized according to commonly known chemical methods. In another embodiment, the oligonucleotide can be obtained from a commercial supplier. The oligonucleotide can include, but is not limited to, at least one nucleotide analog, such as bromo derivatives, azido derivatives, fluorescent derivatives or a combination thereof. Nucleotide analogs are well known to those of skill in the art. The oligonucleotide can include a chain terminator. The oligonucleotide can also be used, e.g., as a cross-linking reagent or a fluorescent tag. Many common linkages can be employed to couple an oligonucleotide to another moiety, e.g., phosphate, hydroxyl, etc. Additionally, a moiety may be linked to the oligonucleotide through a nucleotide analog incorporated into the oligonucleotide. In another embodiment, the oligonucleotide can include a phosphodiester linked 3'-5' and 5'-3' oligonucleotide backbone. Alternatively, the oligonucleotide can include non-phosphodiester linkages, such as phosphotioate type, phosphoramidate and peptide-nucleotide backbones. In another embodiment, moieties can be linked to the backbone sugars of the oligonucleotide. Methods of creating such linkages are well known to those of skill in the art.

Nucleotide and nucleoside analogues are well known on the art. Examples of such nucleoside analogs include, but are not limited to, Cytovene® (Roche Laboratories), Epivir® (Glaxo Wellcome), Gemzar® (Lilly), Hivid® (Roche Laboratories), Rebetron® (Schering), Videx® (Bristol-Myers Squibb), Zerit® (Bristol-Myers Squibb), and Zovirax® (Glaxo Wellcome). See, *Physician's Desk Reference*, 2005 Edition.

Polypeptides acting as additional bioactive agents attached to the polymers in the invention stent coverings and other medical devices can have any suitable length. Specifically, the polypeptides can be about 2 to about 5,000 amino acids in length, inclusive; about 2 to about 2,000 amino acids in length, inclusive; about 2 to about 1,000 amino acids in length, inclusive; or about 2 to about 100 amino acids in length, inclusive.

In one embodiment, the additional bioactive agent polypeptide attached to the polymer coatings for the invention medical devices can be an antibody. In one embodiment, the antibody can bind to a cell adhesion molecule, such as a cadherin, integrin or selectin. In another embodiment, the antibody can bind to an extracellular matrix molecule, such as collagen, elastin, fibronectin or laminin. In still another embodiment, the antibody can bind to a receptor, such as an adrenergic receptor, B-cell receptor, complement receptor, cholinergic receptor, estrogen receptor, insulin receptor, low-density lipoprotein receptor, growth factor receptor or T-cell receptor. Antibodies attached to polymers (either directly or by a linker) in the invention medical devices can also bind to platelet aggregation factors (e.g., fibrinogen), cell proliferation factors (e.g., growth factors and cytokines), and blood clotting factors (e.g., fibrinogen). In another embodiment, an antibody can be conjugated to an active agent, such as a toxin. In another embodiment, the antibody can be Abciximab (ReoProR)). Abciximab is an Fab fragment of a chimeric antibody that binds to beta(3) integrins. Abciximab is specific for platelet glycoprotein IIb/IIIa receptors, e.g., on blood cells. Human aortic smooth muscle cells express alpha(v)beta(3) integrins on their surface. Treating beta(3) expressing smooth muscle cells may prohibit adhesion of other cells and decrease cellular migration or proliferation, thus reducing restenosis following percutaneous coronary interventions (CPI) e.g., stenosis, angioplasty, stenting. Abciximab also inhibits aggregation of blood platelets.

In one embodiment, the peptide can be a glycopeptide. "Glycopeptide" refers to oligopeptide (e.g. heptapeptide) antibiotics, characterized by a multi-ring peptide core optionally substituted with saccharide groups, such as vancomycin. Examples of glycopeptides included in this definition may be found in "Glycopeptides Classification, Occurrence, and Discovery," by Raymond C. Rao and Louise W. Crandall, ("Bioactive agents and the Pharmaceutical Sciences" Volume 63, edited by Ramakrishnan Nagarajan, published by Marcal Dekker, Inc.). Additional examples of glycopeptides are disclosed in U.S. Pat. Nos. 4,639,433; 4,643,987; 4,497,802; 4,698,327, 5,591,714; 5,840,684; and 5,843,889; in EP 0 802 199; EP 0 801 075; EP 0 667 353; WO 97/28812; WO 97/38702; WO 98/52589; WO 98/52592; and in *J. Amer. Chem. Soc.*, 1996, 118, 13107-13108; *J. Amer. Chem. Soc.*, 1997, 119, 12041-12047; and *J. Amer. Chem. Soc.*, 1994, 116, 4573-4590. Representative glycopeptides include those identified as A477, A35512, A40926, A41030, A42867, A47934, A80407, A82846, A83850, A84575, AB-65, Actaplanin, Actinoidin, Ardacin, Avoparcin, Azureomycin, Balhimyein, Chloroorientiein, Chloropolysporin, Decaplanin, -demethylvancomycin, Eremomycin, Galacardin, Helvecardin, Izupeptin, Kibdelin, LL-AM374, Mannopeptin, MM45289, MM47756, MM47761, MM49721, MM47766, MM55260, MM55266, MM55270, MM56597, MM56598, OA-7653, Orenticin, Parvodicin, Ristocetin, Ristomycin, Synmonicin, Teicoplanin, UK-68597, UD-69542, UK-72051, Vancomycin, and the like. The term "glycopeptide" or "glycopeptide antibiotic" as used herein is also intended to include the general class of glycopeptides disclosed above on which the sugar moiety is absent, i.e. the aglycone series of glycopeptides. For example, removal of the disaccharide moiety appended to the phenol on vancomycin by mild hydrolysis gives vancomycin aglycone. Also included within the scope of the term "glycopeptide antibiotics" are synthetic derivatives of the general class of glycopeptides disclosed above, included alkylated and acylated derivatives. Additionally, within the scope of this term are glycopeptides that have been further appended with additional saccharide residues, especially aminoglycosides, in a manner similar to vancosamine.

The term "lipidated glycopeptide" refers specifically to those glycopeptide antibiotics that have been synthetically modified to contain a lipid substituent. As used herein, the term "lipid substituent" refers to any substituent contains 5 or more carbon atoms, preferably, 10 to 40 carbon atoms. The lipid substituent may optionally contain from 1 to 6 heteroatoms selected from halo, oxygen, nitrogen, sulfur, and phosphorous. Lipidated glycopeptide antibiotics are well known in the art. See, for example, in U.S. Pat. Nos. 5,840,684, 5,843,889, 5,916,873, 5,919,756, 5,952,310, 5,977,062, 5,977,063, EP 667, 353, WO 98/52589, WO 99/56760, WO 00/04044, WO 00/39156, the disclosures of which are incorporated herein by reference in their entirety.

Anti-inflammatory agents useful for attachment to polymer coatings of the invention stents and other medical devices, or for loading into the outer layer of the invention multilayered stents include, e.g. analgesics (e.g., NSAIDS and salicyclates), antirheumatic agents, gastrointestinal agents, gout preparations, hormones (glucocorticoids), nasal preparations, ophthalmic preparations, otic preparations (e.g., antibiotic and steroid combinations), respiratory agents, and skin & mucous membrane agents. See, *Physician's Desk Reference,* 2005 Edition. Specifically, the anti-inflammatory agent can include dexamethasone, which is chemically designated as (11θ, 16I)-9-fluro-11,17,21-trihydroxy-16-methylpregna-1,4-diene-3,20-dione. Alternatively, the anti-inflammatory agent can include sirolimus (rapamycin), which is a triene macrolide antibiotic isolated from *Steptomyces hygroscopicus*.

Anti-platelet or anti-coagulation agents include, e.g., Coumadin® (DuPont), Fragmin® (Pharmacia & Upjohn), Heparin® (Wyeth-Ayerst), Lovenox®, Normiflo®, Orgaran® (Organon), Aggrastat® (Merck), Agrylin® (Roberts), Ecotrin® (Smithkline Beecham), Flolan® (Glaxo Wellcome), Halfprin® (Kramer), Integrillin® (COR Therapeutics), Integrillin® (Key), Persantine® (Boehringer Ingelheim), Plavix® (Bristol-Myers Squibb), ReoPro® (Centecor), Ticlid® (Roche), Abbokinase® (Abbott), Activase® (Genentech), Eminase® (Roberts), and Strepase® (Astra). See, *Physician's Desk Reference,* 2005 Edition. Specifically, the anti-platelet or anti-coagulation agent can include trapidil (avantrin), cilostazol, heparin, hirudin, or ilprost.

Trapidil is chemically designated as N,N-dimethyl-5-methyl-[1,2,4]triazolo[1,-5-a]pyrimidin-7-amine.

Cilostazol is chemically designated as 6-[4-(1-cyclohexyl-1H-tetrazol-5-yl)-butoxy]-3,4-dihydro-2(1H)-quinolinone.

Heparin is a glycosaminoglycan with anticoagulant activity; a heterogeneous mixture of variably sulfonated polysaccharide chains composed of repeating units of D-glucosamine and either L-iduronic or D-glucuronic acids.

Hirudin is an anticoagulant protein extracted from leeches, e.g., *Hirudo medicinalis*.

Iloprost is chemically designated as 5-[Hexahydro-5-hydroxy-4-(3-hydroxy-4-methyl-1-octen-6-ynyl)-2(1H)-pentalenylidene]pentanoic acid.

The immune suppressive agent can include, e.g., Azathioprine® (Roxane), BayRho-D® (Bayer Biological), CellCept® (Roche Laboratories), Imuran® (Glaxo Wellcome), MiCRhoGAM® (Ortho-Clinical Diagnostics), Neoran® (Novartis), Orthoclone OKT3® (Ortho Biotech), Prograf® (Fujisawa), PhoGAM® (Ortho-Clinical Diagnostics), Sandimmune® (Novartis), Simulect® (Novartis), and Zenapax® (Roche Laboratories).

Specifically, the immune suppressive agent can include rapamycin or thalidomide. Rapamycin is a triene macrolide isolated from *Streptomyces hygroscopicus*.

Thalidomide is chemically designated as 2-(2,6-dioxo-3-piperidinyl)-1H-iso-indole-1,3(2H)-dione.

Anti-cancer or anti-cell proliferation agents that can be used as an additional bioactive agent, for example, in the outer layer of the invention multilayered stents include, e.g., nucleotide and nucleoside analogs, such as 2-chloro-deoxyadenosine, adjunct antineoplastic agents, alkylating agents, nitrogen mustards, nitrosoureas, antibiotics, antimetabolites, hormonal agonists/antagonists, androgens, antiandrogens, antiestrogens, estrogen & nitrogen mustard combinations, gonadotropin releasing hormone (GNRH) analogues, progestrins, immunomodulators, miscellaneous antineoplastics, photosensitizing agents, and skin and mucous membrane agents. See, *Physician's Desk Reference,* 2005 Edition.

Suitable adjunct antineoplastic agents include Anzemet® (Hoeschst Marion Roussel), Aredia® (Novartis), Didronel® (MGI), Diflucan® (Pfizer), Epogen® (Amgen), Ergamisol® (Janssen), Ethyol® (Alza), Kytril® (SmithKline Beecham), Leucovorin® (Immunex), Leucovorin® (Glaxo Wellcome), Leucovorin® (Astra), Leukine® (Immunex), Marinol® (Roxane), Mesnex® (Bristol-Myers Squibb Oncology/Immunology), Neupogen (Amgen), Procrit® (Ortho Biotech), Salagen® (MGI), Sandostatin® (Novartis), Zinecard® (Pharmacia and Upjohn), Zofran® (Glaxo Wellcome) and Zyloprim® (Glaxo Wellcome).

Suitable miscellaneous alkylating agents include Myleran® (Glaxo Wellcome), Paraplatin® (Bristol-Myers Squibb Oncology/Immunology), Platinol® (Bristol-Myers Squibb Oncology/Immunology) and Thioplex® (Immunex).

Suitable nitrogen mustards include Alkeran® (Glaxo Wellcome), Cytoxane® (Bristol-Myers Squibb Oncology/Immunology), Ifex® (Bristol-Myers Squibb Oncology/Immunology), Leukeran® (Glaxo Wellcome) and Mustargen® (Merck).

Suitable nitrosoureas include BiCNU® (Bristol-Myers Squibb Oncology/Immunology), CeeNU® (Bristol-Myers Squibb Oncology/Immunology), Gliadel® (Rhone-Poulenc Rover) and Zanosar® (Pharmacia and Upjohn).

Suitable antibiotics include Adriamycin PFS/RDF® (Pharmacia and Upjohn), Blenoxane® (Bristol-Myers Squibb Oncology/Immunology), Cerubidine® (Bedford), Cosmegen® (Merck), DaunoXome® (NeXstar), Doxil® (Sequus), Doxorubicin Hydrochloride® (Astra), Idamycin® PFS (Pharmacia and Upjohn), Mithracin® (Bayer), Mitamycin® (Bristol-Myers Squibb Oncology/Immunology), Nipen® (SuperGen), Novantrone® (Immunex) and Rubex® (Bristol-Myers Squibb Oncology/Immunology).

Suitable antimetabolites include Cytostar-U®) (Pharmacia and Upjohn), Fludara® (Berlex), Sterile FUDR® (Roche Laboratories), Leustatin® (Ortho Biotech), Methotrexate® (Immunex), Parinethol® (Glaxo Wellcome), Thioguanine® (Glaxo Wellcome) and Xeloda® (Roche Laboratories).

Suitable androgens include Nilandron® (Hoechst Marion Roussel) and Teslac® (Bristol-Myers Squibb Oncology/Immunology).

Suitable antiandrogens include Casodex® (Zeneca) and Eulexin® (Schering).

Suitable antiestrogens include Arimidex® (Zeneca), Fareston® (Schering), Femara® (Novartis) and Nolvadex® (Zeneca).

Suitable estrogen and nitrogen mustard combinations include Emcyt® (Pharmacia and Upjohn).

Suitable estrogens include Estrace® (Bristol-Myers Squibb) and Estrab® (Solvay).

Suitable gonadotropin releasing hormone (GNRH) analogues include Leupron Depot® (TAP) and Zoladex® (Zeneca).

Suitable progestins include Depo-Provera® (Pharmacia and Upjohn) and Megace® (Bristol-Myers Squibb Oncology/Immunology).

Suitable immunomodulators include Erganisol® (Janssen) and Proleukin® (Chiron Corporation).

Suitable miscellaneous antineoplastics include Camptosar® (Pharmacia and Upjohn), Celestone® (Schering), DTIC-Dome® (Bayer), Elspar® (Merck), Etopophos® (Bristol-Myers Squibb Oncology/Immunology), Etopoxide® (Astra), Gemzar® (Lilly), Hexalen® (U.S. Bioscience), Hycantin® (SmithKline Beecham), Hydrea® (Bristol-Myers Squibb Oncology/Immunology), Hydroxyurea®

(Roxane), Intron A® (Schering), Lysodren® (Bristol-Myers Squibb Oncology/Immunology), Navelbine® (Glaxo Wellcome), Oncaspar® (Rhone-Poulenc Rover), Oncovin® (Lilly), Proleukin® (Chiron Corporation), Rituxan® (IDEC), Rituxan® (Genentech), Roferon-A® (Roche Laboratories), Taxol® (paclitaxol/paclitaxel, Bristol-Myers Squibb Oncology/Immunology), Taxotere® (Rhone-Poulenc Rover), TheraCys® (Pasteur Merieux Connaught), Tice BCG® (Organon), Velban® (Lilly), VePesid® (Bristol-Myers Squibb Oncology/Immunology), Vesanoid® (Roche Laboratories) and Vumon® (Bristol-Myers Squibb Oncology/Immunology).

Suitable photosensitizing agents include Photofrin® (Sanofi).

Specifically, the anti-cancer or anti-cell proliferation agent can include Taxol® (paclitaxol), a nitric oxide-like compound, or NicOX (NCX-4016). Taxol® (paclitaxol) is chemically designated as 5β,20-Epoxy-1,2α4,7β,10β,13α-hexahydroxytax-11-en-9-one 4,10-diacetate 2-benzoate 13-ester with (2R,3S)—N-benzoyl-3-phenylisoserine.

A nitric oxide-like agent includes any bioactive agent that contains a nitric oxide releasing functional group. Suitable nitric oxide-like compounds are S-nitrosothiol derivative (adduct) of bovine or human serum albumin and as disclosed, e.g., in U.S. Pat. No. 5,650,447. See, e.g., David Marks et al., "Inhibition of neointimal proliferation in rabbits after vascular injury by a single treatment with a protein adduct of nitric oxide," *J Clin. Invest*. (1995) 96:2630-2638. NCX-4016 is chemically designated as 2-acetoxy-benzoate 2-(nitroxymethyl)-phenyl ester, and is an antithrombotic agent.

It is appreciated that those skilled in the art understand that the bioactive agent or additional bioactive agent useful in the present invention is the bioactive substance present in any of the bioactive agents or agents disclosed above. For example, Taxol® is typically available as an injectable, slightly yellow viscous solution. The bioactive agent, however, is a crystalline powder with the chemical name 5β,20-Epoxy-1,2α,4,7β,10β,13α-hexahydroxytax-11-en-9-one 4,10-diacetate 2-benzoate 13-ester with (2R,3S)—N-benzoyl-3-phenylisoserine. *Physician's Desk Reference (PDR)*, Medical Economics Company (Montvale, N.J.), (53rd Ed.), pp. 1059-1067.

As used herein a "residue of a bioactive agent" or "residue of an additional bioactive agent" is a radical of such bioactive agent as disclosed herein having one or more open valences. Any synthetically feasible atom or atoms of the bioactive agent can be removed to provide the open valence, provided bioactivity is substantially retained when the radical is attached to a residue of a polymer described herein. Based on the linkage that is desired, those skilled in the art can select suitably functionalized starting materials that can be derived from a bioactive agent using procedures that are known in the art.

The residue of a bioactive agent or additional bioactive agent, as described herein, can be formed employing any suitable reagents and reaction conditions. Suitable reagents and reaction conditions are disclosed, e.g., in *Advanced Organic Chemistry, Part B: Reactions and Synthesis*, Second Edition, Carey and Sundberg (1983); *Advanced Organic Chemistry, Reactions, Mechanisms and Structure*, Second Edition, March (1977); and *Comprehensive Organic Transformations*, Second Edition, Larock (1999).

In certain embodiments, the polymer-bioactive agent linkage can degrade to provide a suitable and effective amount of free bioactive agent. As will be appreciated by those of skill in the art, depending upon the chemical and therapeutic properties of the biological agent, in certain other embodiments, the bioactive agent attached to the polymer performs its therapeutic effect while still attached to the polymer, such as is the case with the "sticky" polypeptides Protein A and Protein G, known herein as "bioligands", which function while attached to the polymer to hold a target molecule close to the polymer, and the bradykinins and antibodies, which function by contacting (e.g., bumping into) a receptor on a target molecule. Any suitable and effective amount of bioactive agent can be released and will typically depend, e.g., on the specific polymer, bioactive agent, and polymer/bioactive agent linkage chosen. Typically, up to about 100% of the bioactive agent can be released from the polymer by degradation of the polymer/bioactive agent linkage. Specifically, up to about 90%, up to 75%, up to 50%, or up to 25% of the bioactive agent can be released from the polymer. Factors that typically affect the amount of the bioactive agent that is released from the polymer is the type of polymer/bioactive agent linkage, and the nature and amount of additional substances present in the formulation.

The polymer-bioactive agent linkage can degrade over a period of time to provide time release of a suitable and effective amount of bioactive agent. Any suitable and effective period of time can be chosen. Typically, the suitable and effective amount of bioactive agent can be released in about twenty-four hours, in about seven days, in about thirty days, in about ninety days, or in about one hundred and twenty days. Factors that typically affect the length of time in which the bioactive agent is released from the polymer-bioactive agent include, e.g., the nature and amount of polymer, the nature and amount of bioactive agent, the nature of the polymer/bioactive agent linkage, and the nature and amount of additional substances present in the formulation.

Polymer Intermixed with Bioactive Agent or Additional Bioactive Agent In addition to being linked to one or more bioactive agents, either directly or through a linker, a polymer used for coating a medical device or making a sheath for a stent structure as described herein can be physically intermixed with one or more bioactive agents or additional bioactive agents to provide a polymer formulation that is used for coating a medical device or a stent structure.

As used herein, "intermixed" refers to a polymer of the present invention physically mixed with a bioactive agent or a polymer as described herein that is physically in contact with a bioactive agent.

As used herein, a "formulation" refers to a polymer as described herein that is intermixed with one or more bioactive agents or additional bioactive agents. The formulation includes such a polymer having one or more bioactive agents present on the surface of the polymer, partially embedded in the polymer, or completely embedded in the polymer. Additionally, the formulation includes a polymer as described herein and a bioactive agent forming a homogeneous composition (i.e., a homogeneous formulation).

By contrast, in the invention multilayered stents, in the outer layer non-covalently bound bioactive agents and/or additional bioactive agents can be intermingled with or "loaded into" any biocompatible biodegradable polymer as is known in the art since the outer layer in this embodiment of the invention does not come into contact with blood. However, the inner layer has only bioactive agents covalently attached to a hydrophilic, blood-compatible polymer as described herein.

Any suitable amount of polymer and bioactive agent can be employed to provide the formulation. The polymer can be present in about 0.1 wt. % to about 99.9 wt. % of the formulation. Typically, the polymer can be present above about 25 wt. % of the formulation; above about 50 wt. % of the formulation; above about 75 wt. % % of the formulation; or above about 90 wt. % of the formulation. Likewise, the bioactive agent can be present in about 0.1 wt. % to about 99.9 wt. % of the formulation. Typically, the bioactive agent can be present above about 5 wt. % of the formulation; above about 10 wt. % of the formulation; above about 15 wt. % of the formulation; or above about 20 wt. % of the formulation.

In yet another embodiment of the invention the polymer coating having a bioactive agent dispersed therein can be applied as a polymeric film onto at least a portion of the surface of any medical device to be implanted into a diabetic that is exposed to blood and upon which it is desirable to establish an endothelial layer (e.g., a heart valve, or a synthetic bypass artery). The polymeric film can have any suitable thickness on the medical device. For example, the thickness of the polymeric film on the medical device can be about 1 to about 50 microns thick or about 5 to about 20 microns thick. In the invention stents and multilayered stents, each of the layers can be from 0.1 micron to 50 microns thick, for example from 0.5 micron to 5 microns in thickness.

The polymeric film can effectively serve as a bioactive agent-eluting polymeric coating on a medical device, such as a stent structure. This bioactive agent eluting polymeric coating can be created on the medical device by any suitable coating process, e.g., dip coating, vacuum depositing, or spray coating the polymeric film, on the medical device. Additionally, the bioactive agent eluting polymer coating system can be applied onto the surface of a stent, a vascular delivery catheter, a delivery balloon, a separate stent cover sheet configuration, or a stent bioactive agent delivery sheath, as described herein to create a type of local bioactive agent delivery system. When the polymer is used as a cover sheet for a stent, the polymer can be processed, for example by extrusion or spinning as is known in the art, to form a woven sheet or mat of fine polymer fibers to which the bioligand is covalently attached, either directly or by means of a linker, as described herein.

The bioactive agent-eluting polymer coated stents and other medical devices can be used in conjunction with, e.g., hydrogel-based bioactive agent delivery systems. For example, in one embodiment, the above-described polymer coated stents and medical devices, can be coated with an additional formulation layer applied over the polymer coated stent surface as a sandwich type of configuration to deliver to the blood vessels bioactive agents that promote natural re-endothelialization processes and prevent or reduce in-stent restenosis. Such an additional layer of hydrogel-based drug release formulation can comprise various bioactive agents mixed with hydrogels (see, U.S. Pat. No. 5,610,241, which is incorporated by reference herein in its entirety) to provide an elution rate different than that of the polymer-active agent coating on the stent structure or medical device surface.

Any suitable size of polymer and bioactive agent can be employed to provide such a formulation. For example, the polymer can have a size of less than about $1\times10^{-4}$ meters, less than about $1\times10^{-5}$ meters, less than about $1\times10^{-6}$ meters, less than about $1\times10^{-7}$ meters, less than about $1\times10^{-8}$ meters, or less than about $1\times10^{-9}$ meters.

The formulation can degrade to provide a suitable and effective amount of the bioactive agents. Any suitable and effective amount of bioactive agent can be released and will typically depend, e.g., on the specific formulation chosen. Typically, up to about 100% of the bioactive agent can be released from the formulation. Specifically, up to about 90%, up to 75%, up to 50%, or up to 25% of the bioactive agent can be released from the formulation. Factors that typically affect the amount of the bioactive agent that is released from the formulation include, e.g., the nature and amount of polymer, the nature and amount of bioactive agent, and the nature and amount of additional substances present in the formulation.

The formulation can degrade over a period of time to provide the suitable and effective amount of bioactive agent. Any suitable and effective period of time can be chosen. Typically, the suitable and effective amount of bioactive agent can be released in about twenty-four hours, in about seven days, in about thirty days, in about ninety days, or in about one hundred and twenty days. Factors that typically affect the length of time in which the bioactive agent is released from the formulation include, e.g., the nature and amount of polymer, the nature and amount of bioactive agent, and the nature and amount of additional substances present in the formulation.

The present invention also provides for an invention stent coated with a formulation that includes a polymer as described herein physically intermixed with one or more bioactive agents. The polymer that is present in the formulation can also be linked, either directly or through a linker, to one or more (e.g., 1, 2, 3, or 4) bioactive agents. As such, the polymer can be intermixed with one or more (e.g., 1, 2, 3, or 4) bioactive agents and can be linked, either directly or through a linker, to one or more (e.g., 1, 2, 3, or 4) bioactive agents.

A polymer used in making an invention stent can include one or more bioactive agents. In one embodiment, the polymer is physically intermixed with one or more bioactive agents. In another embodiment, the polymer is linked to one or more bioactive agents, either directly or through a linker. In another embodiment, the polymer is linked to one or more bioactive agents, either directly or through a linker, and the resulting polymer can also be physically intermixed with one or more bioactive agents.

A polymer used in making an invention stent, whether or not present in a formulation as described herein, whether or not linked to a bioactive agent as described herein, and whether or not intermixed with a bioactive agent as described herein, can also be used in medical therapy or medical diagnosis. For example, the polymer can be used in the manufacture of a medical device. Suitable medical devices include, e.g., artificial joints, artificial bones, cardiovascular medical devices, stents, shunts, medical devices useful in angioplastic therapy, artificial heart valves, artificial by-passes, sutures, artificial arteries, vascular delivery catheters, drug delivery balloons, separate tubular stent cover sheet configurations (referred to herein as "sheaths"), and stent bioactive agent delivery sleeve types for local bioactive agent delivery systems.

In still another embodiment, the invention provides methods for treating a patient suffering from diabetes having a vessel with a damaged endothelium by implanting an invention stent in the vessel at the locus of damage and allowing the stent to interact with blood components within the vessel. The invention may further comprise testing a blood sample from the diabetic patient to determine the amount of therapeutic PECs in the sample as compared with a parallel sample of blood from a healthy non-diabetic individual to detect a decrease in the amount of therapeutic PECs in the blood from the diabetic patient. Such testing may be conducted prior to implantation of an invention stent to determine whether the diabetic patient has a decreased amount or concentration of therapeutic PECs as compared with the normal concentration in healthy non-diabetic patients.

In another embodiment, the invention methods for treating diabetics having damaged vasculature may further comprise obtaining therapeutic PECs from the circulating blood of the diabetic, expanding the patient's therapeutic PECs ex vivo, and transfusing the autologous PECs into the circulating blood of the diabetic patient either before or contemporaneously with implantation of the invention stents.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

The invention will be further understood with reference to the following examples, which are purely exemplary, and should not be taken as limiting the true scope of the present invention as described in the claims.

EXAMPLE 1

Amide Bond Formation—This example illustrates the coupling of a carboxyl group of a polymer with an amino functional group of the bioactive agent, or equally, the coupling of a carboxyl group of the bioactive agent with an amino functional group of a polymer.

Coupling Through Pre-Formed Active Esters; Carbodiimide Mediated Couplings—Conjugation of 4-Amino-Tempo to Polymer The free carboxylic acid form of the PEA polymer is converted first to its active succinimidyl ester (PEA-OSu) or benzotriazolyl ester (PEA-OBt). This conversion can be achieved by reacting dried PEA-H polymer with N-Hydroxysuccinimide (NHS) or 1-Hydroxybenzotriazole (HOBt) and a suitable dehydrating agent, such as dicyclohexylcarbodiimide (DCC), in anhydrous $CH_2Cl_2$ at room temperature for 16 hrs. After filtering away the precipitated dicyclohexylurea (DCU), the PEA-OSu product may be isolated by precipitation, or used without further purification, in which case the PEA-OSu solution is transferred to a round bottom flask, diluted to the desired concentration, and cooled to 0° C. Next, a solution of the free amine-containing bioactive agent—the nucleophile, specifically, 4-Amino-Tempo—in $CH_2Cl_2$ is added in a single shot at 0° C. (Equally, the nucleophile may be revealed in situ by treating the ammonium salt of the bioactive agent with a hindered base, preferably a tertiary amine, such as like triethylamine or, diisopropylethylamine, in a suitable aprotic solvent, such as dichloromethane (DCM)). The reaction is monitored by tracking consumption of the free amine by TLC, as indicated by ninhydrin staining. Work-up for the polymer involves customary precipitation of the reaction solution into a mixture of non-solvent, such as hexane/ethyl acetate. Solvent is then decanted, polymer residue is resuspended in a suitable solvent, filtered, concentrated by roto-evaporation, cast onto a clean teflon tray, and dried under vacuum to furnish the PEA-bioactive agent conjugate, specifically, PEA-4-Amino-Tempo.

Aminium/Uronium Salt and Phosphonium Salt Mediated Couplings Two effective catalysts for this type of coupling include: HBTU, O-(benzotriazol-1-yl)-1,1,3,3-teramethyluronium hexafluorophosphate, and BOP, 1-benzotriazolyoxy-tris(dimethyl-amino)phosphonium hexafluorophosphate (Castro's Reagent). These reagents are employed in the presence of equimolar amounts of the carboxyl group of the polymer and the amino functional group of the bioactive agent (neutral or as the ammonium salt), with a tertiary amine such as diisopropylethylamine, N-methylmorpholine, or dimethyl-substituted pyridines (DMAP), in solvents such as DMF, THF, or acetonitrile.

EXAMPLE 2

Ester Bond Formation—This example illustrates coupling of a carboxyl group of a polymer with a hydroxyl functional group of the bioactive agent, or equally, coupling of a carboxyl group of the bioactive agent with a hydroxyl functional group of a polymer.

Carbodiimide Mediated Esterification For the conjugation, a sample of the carboxyl-group-containing polymer was dissolved in DCM. To this slightly viscous solution was added a solution of the hydroxyl-containing-drug/biologic and DMAP in DCM. The flask was then placed in an ice bath and cooled to 0° C. Next, a solution of 1,3-diisopropylcarbodiimide (DIPC) in DCM was added, the ice bath removed, and the reaction warmed to room temperature. The conjugation reaction was stirred at room temperature for 16 hours during which time TLC was periodically performed to monitor consumption of the hydroxyl functional group of the bioactive agent. After the allotted time, the reaction mixture was precipitated, and the polymer-bioactive agent conjugate was isolated as described above in Example 1.

EXAMPLE 3

Figure 2:
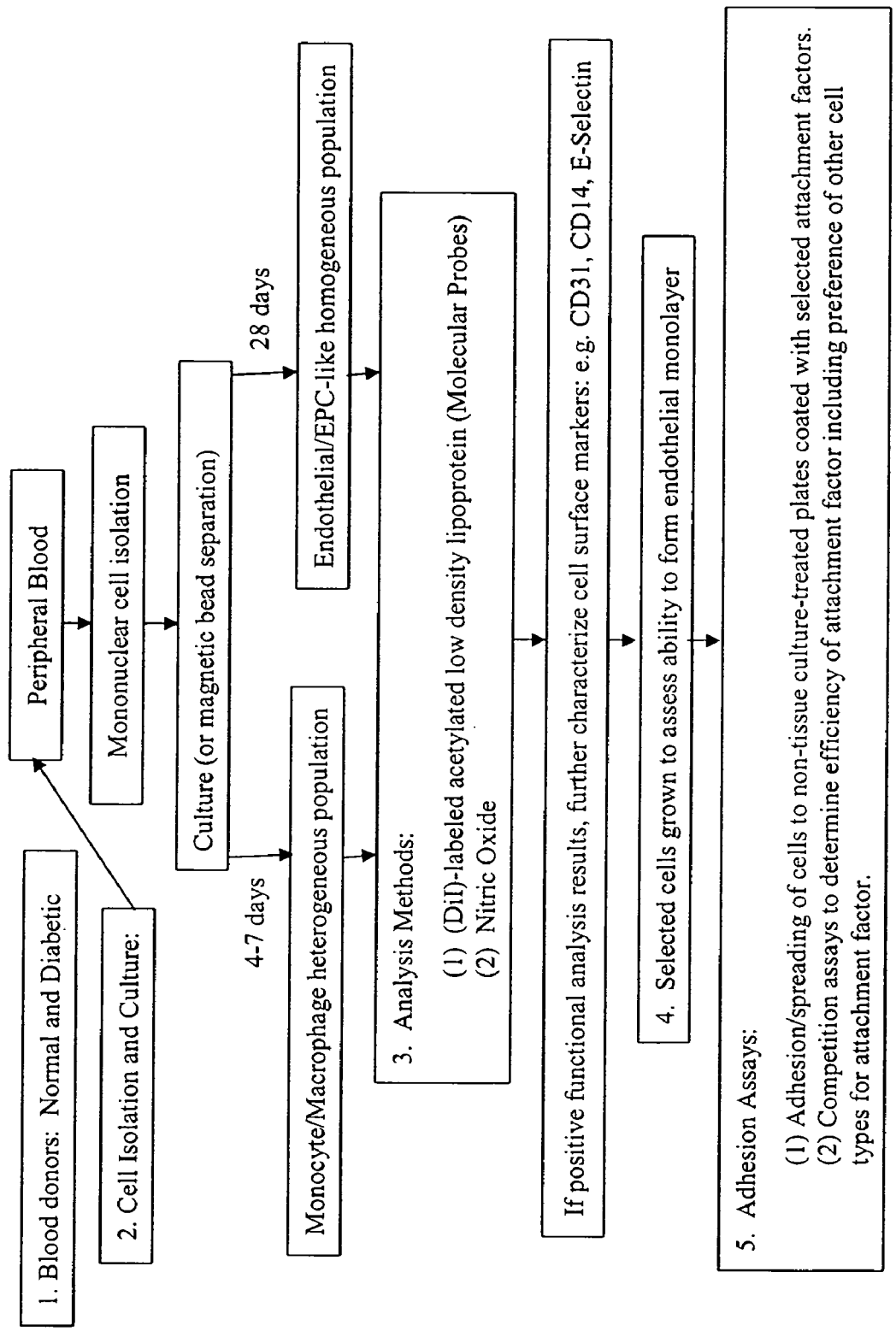
FIG. 2 is a flow chart describing the PEC isolation protocol.

PEC Isolations To establish the protocol for isolating the progenitor endothelial cells (PECs) from peripheral blood, blood from healthy, normal donors was used. A literature review generated multiple PEC isolation protocols (*J.C.I.* (2000) 105:71-77; *Circ.* (2003) 107:143-149; *Circ.* (2003) 107:1164-1169; *Plast. Reconstruc. Surgr.* (2004) 113:284; and *Am. J. Physiol. Heart Circ. Physiol.* (2004) 286:H1985-H1993). Surprisingly, however, preliminary attempts required modification of the known protocols to ensure successful isolations. The flow chart in FIG. 2 presents a modified protocol followed in isolation of PECs.

From a trial PEC isolation, it was determined that cells would attach and grow better on fibronectin-coated plates than on gelatin-coated plates. Cells were isolated from ~120 milliliters of peripheral blood and then single aliquots of cells were plated in Endothelial Basal Medium and 5% FBS (Cambrex). The media was changed every 4-5 days. The total cell number obtained from the isolations was donor-dependent and ranged from 40 million to 200 million cells.

Table 1 below indicates the isolation methods and the PEC isolation outcome for PEC isolation from various donors. Initially, both a mononuclear cell Ficoll gradient protocol (designed to isolate human mononuclear cells from peripheral blood) and a CD133+ magnetic bead purification step were used to ensure the isolation of PECs. It did not appear that the CD133+ purification step was increasing the isolation of PECs, so this step was omitted from the last two donors.

TABLE 1

| Donor Identifier | Gradient | CD133+ | PEC |
|---|---|---|---|
| Donor 1 | Yes | Yes | Yes |
| Donor 2 | Yes | Yes | No |
| Donor 3 | Yes | Yes | No |
| Donor 1 | Yes | Yes | Yes |
| Donor 4 | Yes | No | No |
| Donor 5 | Yes | No | Yes |

Cells were plated either in 12-well or 6-well fibronectin-coated plates and monitored daily, over a span of about 28-30 days. The culture media used in the PEC isolations was Endothelial Basal Medium plus SingleQuot Kit (Cambrex Corporation, East Rutherford, N.J.), a mixture of hydrocortisone, hEGF, FBS, VEGF, hFGF-B, R3-IGF-1, ascorbic acid and heparin. Generally from 10-15 days in culture after the isolation were required before a monolayer became apparent.

Once a monolayer was identified, cells were further characterized with DiI-acetylated-Low Density Lipoprotein (LDL). The human LDL complex delivers cholesterol to cells via receptor-mediated endocytosis. However, the acetylated form of LDL is not taken up by the LDL receptor, but is taken up by macrophages and endothelial cells via a "scavenger" receptor specific for the modified LDL. Decreased uptake by endothelial cells as compared with macrophages was determined by microscope and photographed (100× magnification). The monolayer remains actively growing for a few months. Cells were replated and reformed the monolayer for several passages (about 30 days in culture) before becoming senescent.

The number of circulating PECs is known to be extremely low, below 0.1%; accordingly, the success rate of PEC isolations was found to be about 40%. (Herz (2002) 27: 579-88).

EXAMPLE 4

Cell Recruitment to Bioactive Agents To select appropriate bioligands for use as recruitment factors in stent applications, an in vitro adhesion assay was developed. This assay can distinguish between endothelial cells (ECs) and smooth muscle cells (SMCs) to aid in selecting potential attachment factors. Both the ECs and SMCs used in these assays were purchased from Cambrex (Baltimore, Md.) (HASMC=Human Aortic Smooth Muscle Cells and HCAEC=Human Coronary Artery Endothelial Cells).

Figure 3:
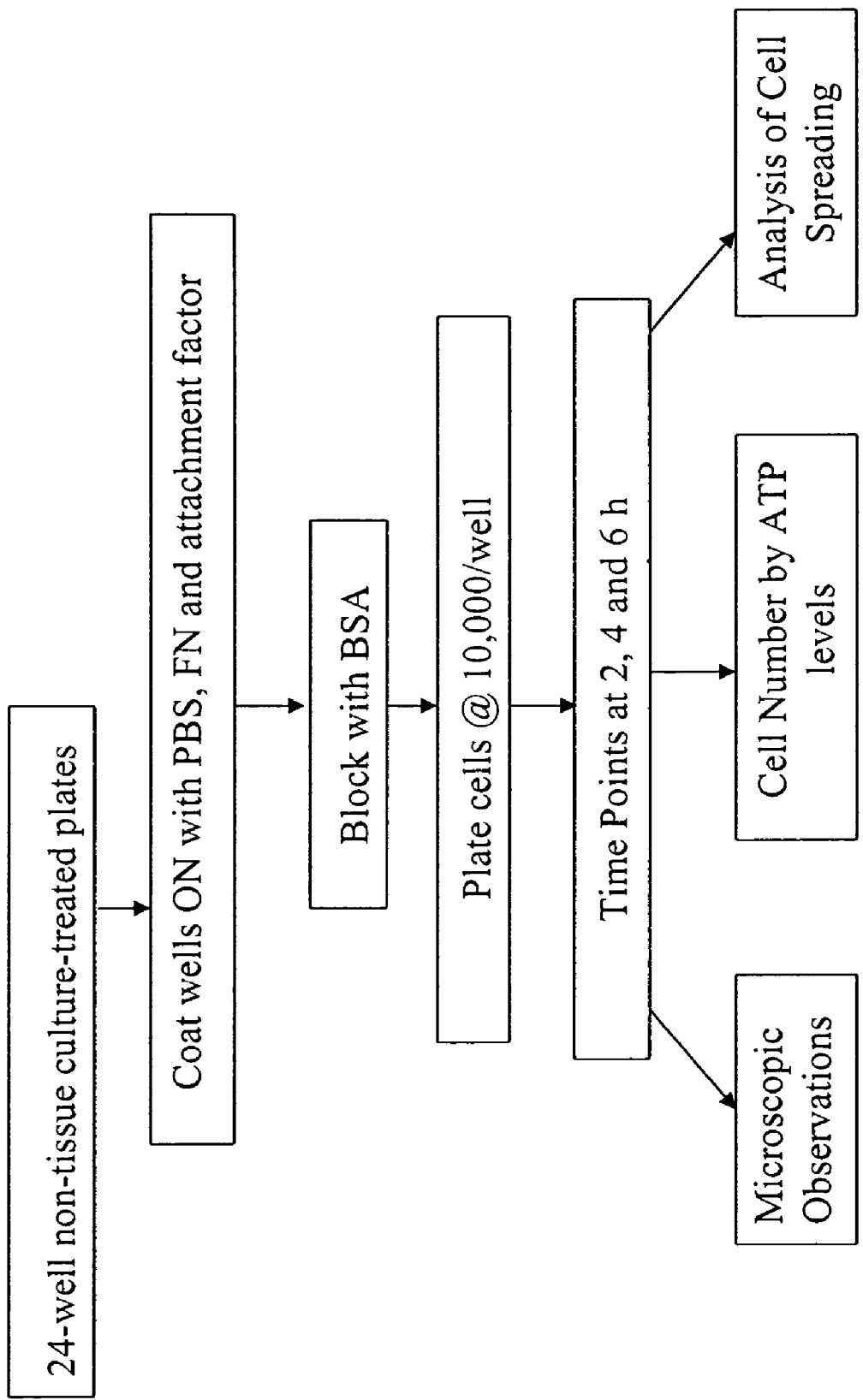
FIG. 3 is a flow chart of the protocol for adhesion assays conducted with ECs and SMCs.

FIG. 3 shows the flow chart of the protocol followed for this assay. The attachment factor, in a phosphate buffered saline (PBS) solution, was coated onto a non-tissue culture dish and allowed to adsorb overnight at 4° C. The following day the plate was blocked for 1 hour at room temperature with heat-inactivated, 0.2% bovine serum albumin (BSA) solution (in PBS) to prevent non-specific attachment. A timed adhesion assay was then conducted. The assay includes negative control wells coated only with PBS and positive control wells coated with fibronectin. So far, none of the adhesion factors tested has surpassed the cell adhesion and cell spreading induced by fibronectin. In addition to adhesion, spreading is also an important consideration in determining the suitability of a substrate. If the cells are not able to spread, it is unlikely that the cells will proliferate on that surface.

Initial efforts focused on potential recruitment factors with low affinity but present in high density. A variety of potential recruitment factors were tested, including:

1. Sialyl Lewis X, a ligand for Selectin receptors found on endothelium;
2. CS5, whose amino acid sequence is Gly-Glu-Glu-Ile-Gln-Ile-Gly-His-Ile-Pro-Arg-Glu-Asp-Val-Asp-Tyr-His-Leu-Tyr-Pro (SEQ ID NO:1). CS5 is found in the Type III connecting segment of fibronectin, an extracellular matrix protein known to bind many different cells, including ECs. The sequence for the CS5 peptide contains the amino acid sequence REDVDY (underlined) (SEQ ID NO:2); and
3. GREDVDY (SEQ ID NO:11), which includes a G linker placed on the REDVDY sequence.)

Of the bioligands tested to date, CS5 and GREDVDY gave the most promising adhesion data with the best sites for conjugation to the polymers used in making the invention stents. Even though neither of these peptide sequences equaled the large molecule fibronectin in cell adhesion or spreading, surprisingly both peptide sequences showed specificity for ECs over SMCs and these small peptide sequences can be readily synthesized and bound to the polymers used in the polymers used in manufacture of the invention stents and implantable medical device coverings.

Figure 4:
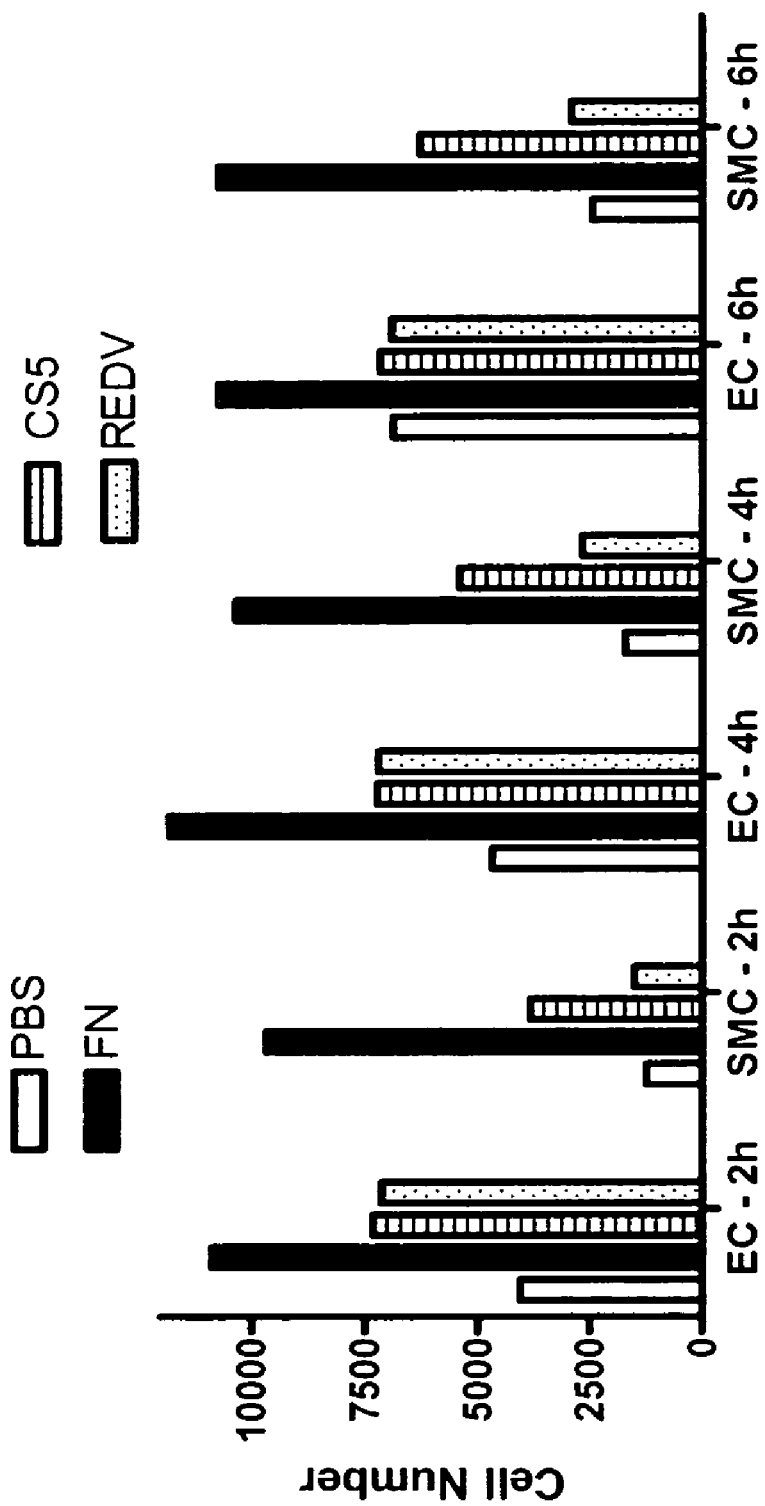
FIG. 4 is a graph summarizing the results of a representative adhesion assay quantitation based on ATP standard curve. At each time point of the adhesion assay, an ATP assay was done to determine the number of adherent cells.

In addition to microscopic observations, cell adhesion was quantitated using an ATP assay. Data of a representative adhesion assay quantitation by ATP standard curve is shown in the graph in FIG. 4, which illustrates the comparative results obtained at 2, 4 and 6 hours into the assay. The assay can identify the number of cells that are adhered to a specific substrate; however, it does not take into consideration cell spreading. The cell spreading determined in microscopic observations may indicate that cell spreading can increase the overall degree of cell adhesion since more space is occupied by a well spread cell than by an adhered cell that has not spread on the surface, due to timing of data points or appropriateness of the substrate used. The ATP data are useful to support the observational findings of the adhesion assay but cannot replace the adhesion assay.

EXAMPLE 5

Figure 5:
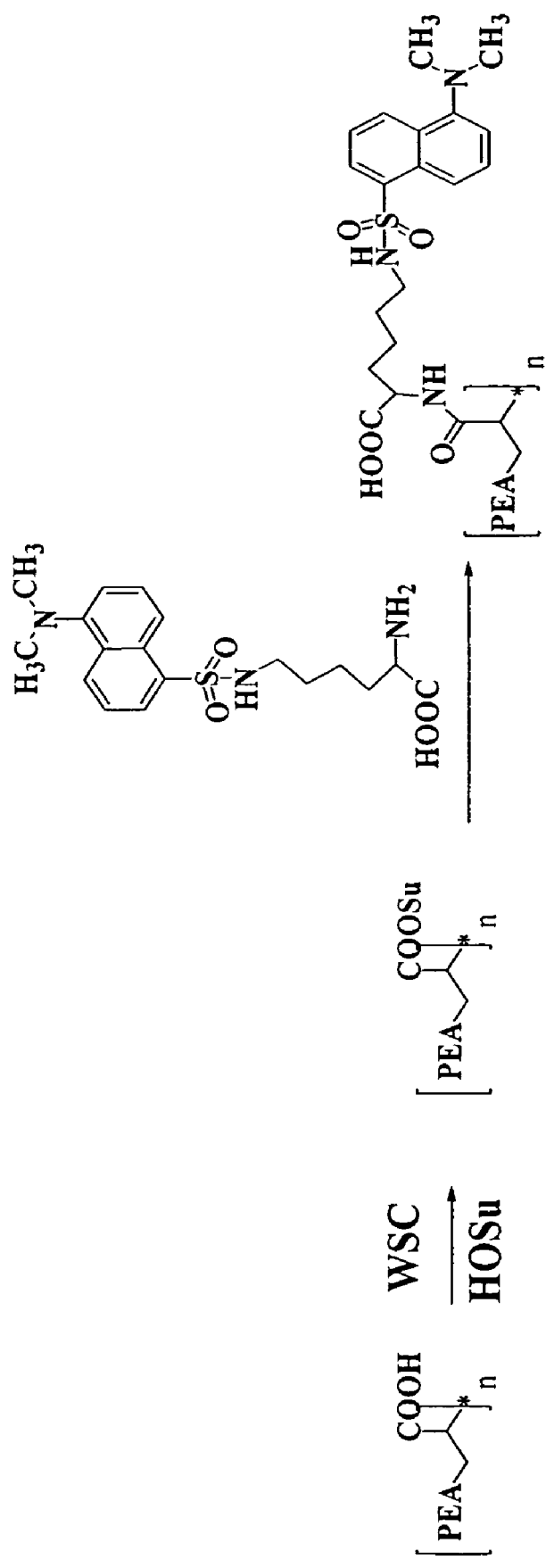
FIG. 5 shows the chemical structure of dansyl, an acronym for 5 dimethylamino-1 naphthalenesulfonyl, a reactive fluorescent dye, linked to PEA.
Figure 6:
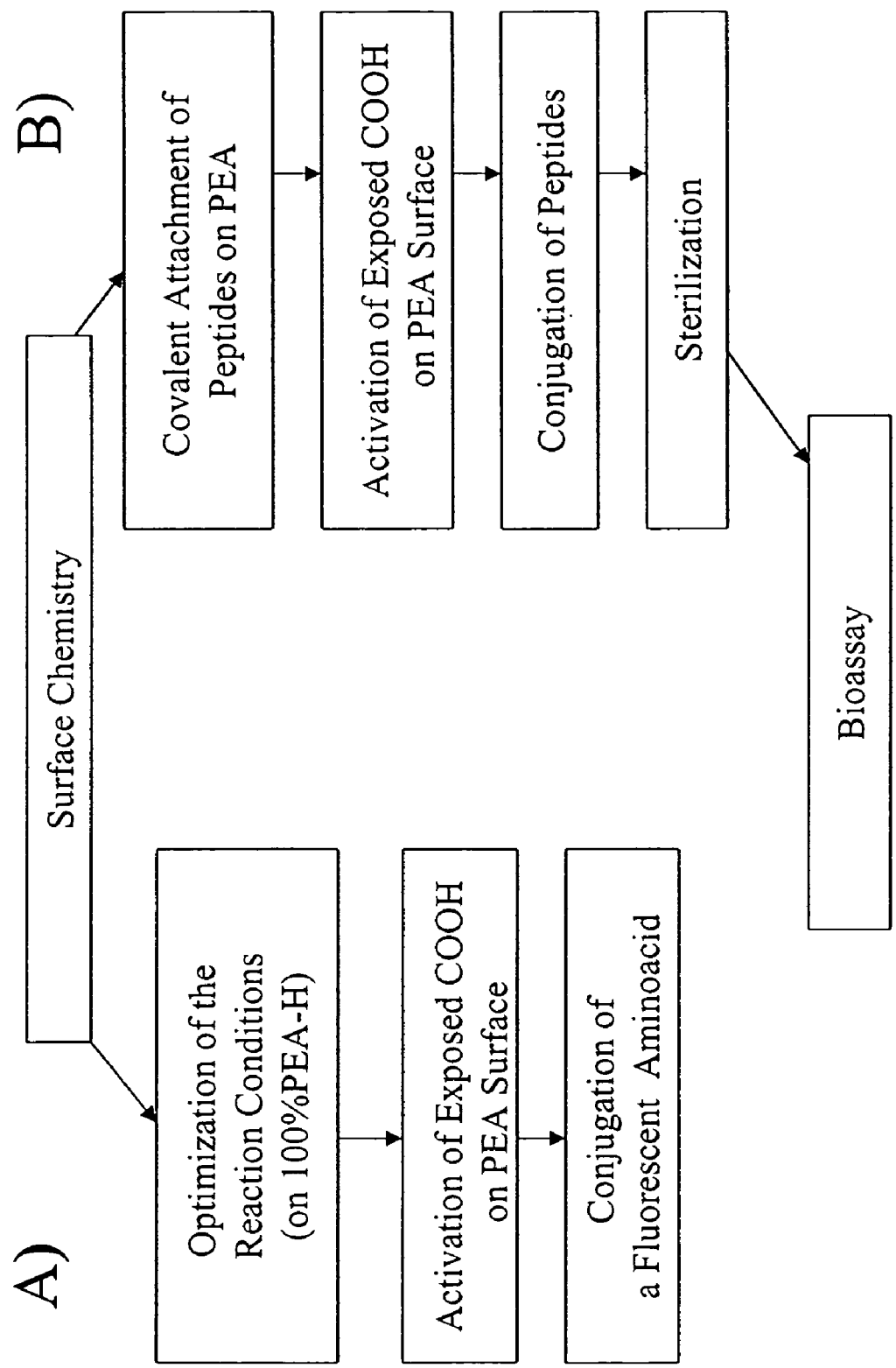
FIGS. 6A-B are flowcharts summarizing surface chemistry optimization protocols.

Cell Recruitment to Bioactive Agent-Polymer Conjugates Based upon the promising results from the adhesion assays, the next step was to conjugate the most effective of the identified recruitment factors to the stent polymer to assess the increased adhesion to the polymer induced with these potential recruitment factors. The first conjugation was done to the PEA-H version of the polymer (acid) since this polymer has suitable sites for conjugation. The peptides can be covalently bound to this polymer via a wide variety of suitable functional groups. For example, when the biodegradable polymer is a poly(ester amide) (PEA) containing Lysine residues, the carboxyl groups from the Lysine residues can be used to react with a complementary moiety on the peptide, such as an hydroxy, amino, thio moiety, and the like (5). Specifically, the PEA-H polymer with free COOH reacts with water soluble carbodiimide (WSC) and N-Hydroxysuccinimide (HOSu) to produce an activated ester, which, in turn, reacts with an amino functional group of a peptide to provide an amide linkage (FIG. 6B). By using a fluorescent dansyl-lysine (FIG. 5), the optimal reaction conditions for activation and conjugation were determined (FIG. 6A).

The conjugation of CS5 and GREDVDY peptides to the polymer was then performed using the same protocol (FIG. 6B). The adhesion assay showed that the conjugation of the peptides did not alter their ability to bind to cells; and, further, that the ECs when compared to the SMCs adhered significantly better to the conjugated peptides than on the unconjugated PEA-H polymer.

A similar protocol (see flow chart FIG. 6B) was used to conjugate combinations of the acid polymer with PEA polymer of structure (I) containing acetylated ends and benzylated COOH groups, (PEA-AcBz) and PEA-TEMPO (50/50 and 10/90), respectively. By combining the conjugatable acid form with the other polymers, a determination could be made whether the presence of the recruitment peptide on the polymer conferred an advantage in EC recruitment.

Microscopic observations taken at 2 h, 4 h and 6 h from duplicate wells from two representative adhesion assays are summarized in Table 2 below.

TABLE 2

Summary of Assays with Conjugated Peptides on Polymer

| Coating/Conj | 50/50 H/Bz 2a & 2b 50/50 H/T 3a & 3b Assay 1 | 50/50 H/Bz 2a & 2b 50/50 H/T 3a & 3b Assay 2 | 10/90 H/Bz 2a & 2b 10/90 H/T 3a & 3b Assay 1 | 10/90 H/Bz 2a & 2b 10/90 H/T 3a & 3b Assay 2 | Plastic Assay 1 | Plastic Assay 2 |
|---|---|---|---|---|---|---|
| 2 h | | | | | | |
| 2A | | | | | | |
| PBS | 20% r | 20-30% r/s | 30% r/s | 30% r/s | 20% r/s | 20–30% r/s/sp |
| Conj CS5 | 20% r | 20-30% r | 30% r/s | 30% r/s | | |
| 2B | | | | | | |
| PBS | 20% | 30% r/s | 30% r | 30% r/s | 20-30% r | 30% r/s |
| Conj REDV | 20-30% r | 30-40% r/s/sp | 30% r/s | 30% r/s/sp | | |
| 3A | | | | | | |
| PBS | 30% r | 20-30% r/s | 30% r/s | 30% r/s | 20-30% r | 20–30% r/s |
| Conj CS5 | 20-30% r/s | 30% r/s | 30% r/s | 30% r/s/sp | | |
| 3B | | | | | | |
| PBS | 20-30% r | 30% r/s/sp | 20-30% r/s | 30% r/s/sp | 20-30% r | 20–30% r/s |
| Conj REDV | 20-30% r | 30% r/s/sp | 30% r/s | 30% r/s/sp | | |
| 4 h | | | | | | |
| 2A | | | | | | |
| PBS | 30% r | 20-30% r | 40% r/s | 30% r/s/sp | 30% r/s | |
| Conj CS5 | 30% r | 30% r/s/sp | 40% r/sp | 30% s/sp | | |
| 2B | | | | | | |
| PBS | 30% r | 30-40% r/s | 30% r/s | 30-40% r/s/sp | 20% r | 30% s/sp |
| Conj REDV | 30% s/sp | 30-40% s/sp | 30-40% r/s/sp | 30-40% s/sp | | |
| 3A | | | | | | |
| PBS | 30% r | 30% r/s | 30% r/s | 30% s/sp | 30% r | 30% r/s |
| Conj CS5 | 30% r | 30-40% r/s/sp | 30% r/s/sp | 30-40% s/sp | | |
| 3B | | | | | | |
| PBS | 30% r | 30% r/s/sp | 30% r/s/sp | 30% s/sp | 30% r | 20–30% r/s/sp |
| Conj REDV | 30% | 30% r/s/sp | 30-40% s/sp | 40% s/sp | | |
| 6 h | | | | | | |
| 2A | | | | | | |
| PBS | 20% r | 20% r/s | 30% r/s | 30% r/s/sp | 20% r/s | 30% r/s/sp |
| Conj CS5 | 20% r | 30% r/s | 30-40% s/sp | 30% r/s/sp | | |
| 2B | | | | | | |
| PBS | 20% r | 30% r/s/sp | 30% r/s/sp | 30-40% r/s/sp | 20% r | 30% r/s/sp |
| Conj REDV | 30% r/s | 30-40% r/s/sp | 30% s/sp | 30-40% r/s/sp | | |
| 3A | | | | | | |
| PBS | 20% r | 30% r/s | 30% r/s/sp | 30-40% r/s/sp | 20% r | 30–40% r/s |
| Conj CS5 | 20% r | 30% r/s | 30-40% r/s/sp | 30% r/s/sp | | |
| 3B | | | | | | |
| PBS | 20% r | 30% r/s | 30% r | 30-40% s/sp | 20% r | 30% r/s |
| Conj REDV | 20% r | 30-40% s/sp | 30-40% r/s/sp | 40% s/sp | | | r = round,
s = spindly,
sp = spread;
50/50 H/Bz = 50% PEA-H and 50% PEA-Ac-Bz;
10/90 H/Bz = 10% PEA-H and 90% PEA-Ac-Bz;
50/50 H/T = 50% PEA-H and 50% PEA-Ac-TEMPO;
10/90 H/T = 10% PEA-H and 90% PEA-Ac-TEMPO.

A complete evaluation of the assays with conjugated peptides on the polymer (Table 2), showed a benefit to the presence of the recruitment peptides on the polymer. The following combinations of polymer conjugated to the GREDVDY peptide resulted in an increased adhesion over basal levels in both assays 1 and 2 (early and late time points). 50/50 PEA-H/PEA-Ac-Bz (H/Bz) and 10/90 PEA-H/PEA-TEMPO (H/T) conjugated to GREDVDY—at middle and late time points. Surprisingly, the shorter peptide (7 mer) proved more robust in cell recruitment than the longer (20 mer) CS5 peptide.

Although the invention has been described with reference to the above examples, it will be understood that modifications and variations are encompassed within the spirit and scope of the invention. Accordingly, the invention is limited only by the following claims.

What is claimed is:

1. A bioactive implantable stent comprising a stent structure with a surface coating of a biodegradable, bioactive polymer, wherein the polymer comprises at least one bioligand covalently bound to the polymer wherein the bioligand binds specifically to integrin receptors on progenitors of endothelial cells (PECs) in circulating blood, and wherein the bioligand has an amino acid sequence as set forth in SEQ ID NO: 1, 2 or 11.

2. The stent of claim 1, wherein the stent structure is porous and the coating is multilayered and encapsulates the stent structure, the multilayered coating comprising:

an outer drug-eluting biodegradable polymer layer, which sequesters an unbound bioactive agent that promotes endogenous healing of epithelium; and an inner layer of the biodegradable, biocompatible polymer with the at least one bioligand covalently bound to the biocompatible biodegradable polymer.

3. The stent of claim 2, further comprising a biodegradable barrier layer lying between and in contact with the outer layer and the inner layer and which barrier layer is impermeable to the bioactive agent.

4. The stent of claim 1, wherein the biodegradable, biocompatible polymer further comprises at least one bioactive agent that promotes production of nitric oxide by endothelial cells at a locus adjacent to the stent.

5. The stent of claim 4, wherein the bioactive agent is selected from bradykinins 1 and 2.

6. The stent of claim 4, wherein the bioactive agent is an aminoxyl.

7. The stent of claim 6, wherein the aminoxyl is 4-amino-2,2,6,6-tetramethylpiperidinyloxy, free radical (4-Amino-TEMPO or 4-hydroxy-TEMPO).

8. The stent of claim 1, wherein the biodegradable, biocompatible polymer comprises at least one amino acid conjugated to at least one non-amino acid moiety per repeat unit.

9. The stent of claim 1, wherein the biodegradable, biocompatible polymer has formula (I):

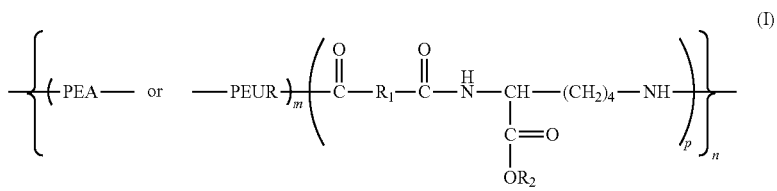

where

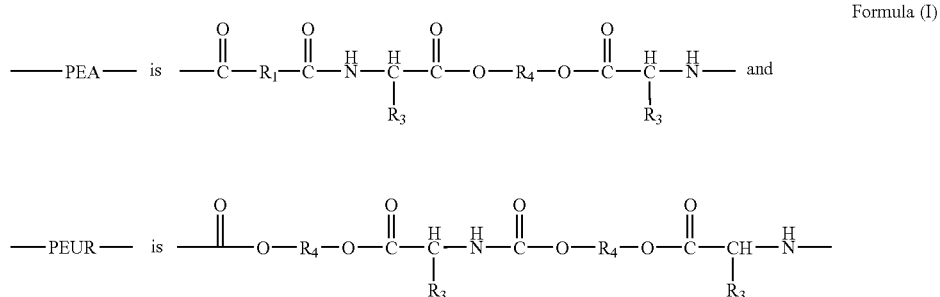

wherein n ranges from about 50 to about 150, m ranges about 0.1 to about 0.9: p ranges from about 0.9 to about 0.1;

$R_1$ is selected from $(C_2-C_{20})$alkylene and $(C_2-C_{20})$alkenylene;

$R_2$ is selected from hydrogen, $(C_6-C_{10})$aryl$(C_1-C_6)$alkyl, and t-butyl;

$R_3$ is selected from hydrogen, $(C_1-C_6)$alkyl, $(C_2-C_6)$alkenyl, $(C_2-C_6)$alkynyl, and $(C_6-C_{10})$aryl$(C_1-C_6)$alkyl; and $R_4$ is selected from $(C_2-C_{20})$alkylene, $(C_2-C_{20})$alkenylene, $(C_2-C_{20})$alkyloxy, and 1,4:3,6-dianhydrohexitols of general formula (II):

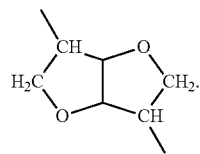

(II)

10. The stent of claim 9, wherein the biodegradable, biocompatible polymer has the chemical of structural formula (I) and $R_3$ is $CH_2Ph$.

11. The stent of claim 9, wherein $R_1$ is selected from —CH═CH—, —CH$_2$—CH═CH—CH$_2$—, —(CH$_2$)$_4$—, —(CH$_2$)$_6$—, and —(CH$_2$)$_8$—.

12. The stent of claim 9, wherein the 1,4:3,6-dianhydrohexitol of general formula (II) is D-glucitol, D-mannitol, or L-iditol.

13. The stent of claim 9, wherein the at least one bioligand is conjugated to the biodegradable, biocompatible polymer on the exterior of the polymer coating.

14. The stent of claim 9, further comprising at least one additional bioactive agent suitable for promoting healing in a damaged artery.

15. The stent of claim 14, wherein there is a total of about 5 to about 150 molecules of the at least one additional bioactive agent per molecule of the biodegradable, biocompatible polymer.

16. The stent of claim 9, wherein the polymer has an average molecular weight in range from about 5,000 to about 300,000.

17. The stent of claim 9, wherein the polymer has from about 5 to about 70 molecules of at least one bioactive agent attached thereto.

18. The stent of claim 9, wherein the biodegradable, biocompatible polymer is contained in a polymer-bioactive agent conjugate having formula (III):

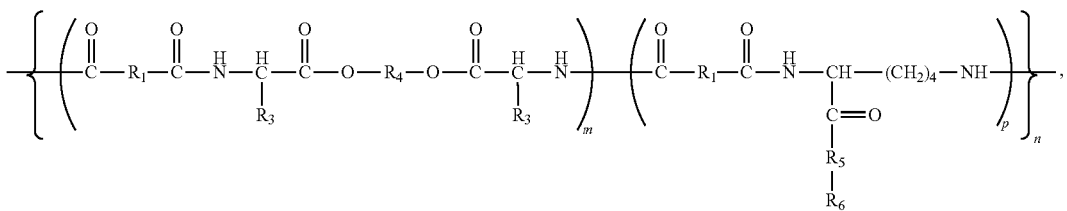

wherein n, m, p, $R_1$, $R_3$, and $R_4$ are as above and, $R_5$ is selected from —O—, —S—, and $NR_8$—, wherein $R_8$ is H or $(C_1-C_8)$ alkyl; and $R_6$ is a bioactive agent.

19. The stent of claim 17, wherein two or more molecules of the biodegradable, biocompatible polymer are crosslinked to provide an —$R_5$—$R_6$—$R_5$— conjugate.

20. The stent of claim 9, wherein a linker separates the bioligand from the biodegradable, biocompatible polymer by about 5 angstroms up to about 200 angstroms.

21. A kit comprising a bioactive implantable stent comprising a stent structure with a surface coating of a biodegradable, bioactive polymer and at least one bioligand covalently bound to the biodegradable, biocompatible polymer, wherein the bioligand binds specifically to a target on therapeutic PECs, and wherein the bioligand has an amino acid sequence as set forth in SEQ ID NO: 1, 2 or 11.

22. The kit of claim 21, wherein the stent structure is porous and the coating is multilayered and encapsulates the stent structure, the multilayered coating comprising:
an outer drug-eluting biodegradable polymer layer, which sequesters an unbound bioactive agent for promoting endogenous endothelial healing; and
an inner layer of the biodegradable, biocompatible polymer with the at least one bioligand covalently bound thereto, wherein the bioligand binds specifically to integrin receptors in PECs.

23. The kit of claim 22, wherein the multilayered coating further comprises a biodegradable barrier layer lying between and in contact with the outer layer and the inner layer and which barrier layer is impermeable to the bioactive agent.

24. A tubular sheath comprising a biodegradable, bioactive polymer, wherein the polymer comprises at least one bioligand covalently bound to the polymer, wherein the bioligand specifically binds to an integrin receptor on PECs, and wherein the bioligand has an amino acid sequence as set forth in SEQ ID NO: 1, 2 or 11.

25. The sheath of claim 24, wherein the biodegradable, bioactive polymer has formula (I):

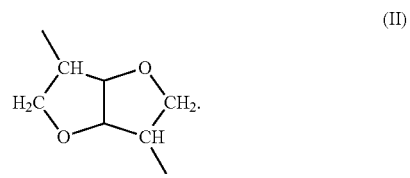

26. The sheath of claim 25, wherein the biodegradable, biocompatible polymer has the chemical of structural formula (I) and $R_3$ is $CH_2Ph$.

27. The sheath of claim 25, wherein $R_1$ is selected from $-CH=CH-$, $-CH_2-CH=CH-CH_2-$, $-(CH_2)_4-$, $-(CH_2)_6-$, and $-(CH_2)_8-$.

28. A method for treating damaged arterial endothelium in the heart or limb in a patient having Type II diabetes, comprising implanting the bioactive implantable stent according to claim 1 to promote natural healing of damaged arterial endothelium in the artery wall of the heart or limb of the patient.

29. The method of claim 28, wherein the damaged arterial endothelium is in the heart of the patient.

30. The method of claim 29, wherein the damaged arterial endothelium is peripheral limb endothelium.

31. An implantable medical device comprising a coating of a biodegradable, bioactive polymer upon at least a portion of a surface thereof, wherein the polymer comprises at least one

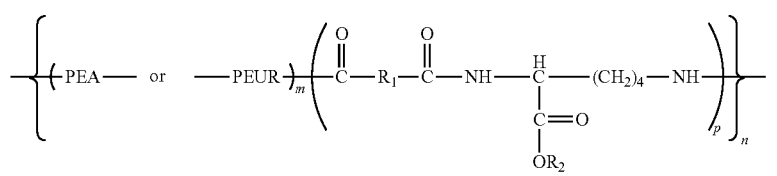

where

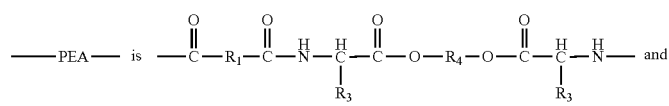

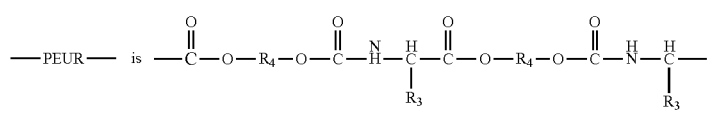

wherein n ranges from about 50 to about 150, m ranges about 0.1 to about 0.9: p ranges from about 0.9 to about 0.1;

$R_1$ is selected from $(C_2-C_{20})$alkylene and $(C_2-C_{20})$alkenylene; $R_2$ is selected from hydrogen, $(C_6-C_{10})$aryl$(C_1-C_6)$alkyl, and t-butyl;

$R_3$ is selected from hydrogen, $(C_1-C_6)$alkyl, $(C_2-C_6)$alkenyl, $(C_2-C_6)$alkynyl, and $(C_6-C_{10})$aryl$(C_1-C_6)$alkyl; and $R_4$ is selected from $(C_2-C_{20})$alkylene, $(C_2-C_{20})$alkenylene, $(C_2-C_{20})$alkyloxy, and 1,4:3,6-dianhydrohexitols of general formula (II):

bioligand covalently bound to the polymer, wherein the bioligand specifically binds an integrin receptor on PECs found in peripheral blood, and wherein the bioligand has an amino acid sequence as set forth in SEQ ID NO: 1, 2 or 11.

32. The implantable medical device of claim 31, wherein the polymer comprises at least one amino acid conjugated to at least one non-amino acid moiety per repeat unit.

33. The implantable medical device of claim 31, wherein the medical device is selected from the group consisting of a stent, a heart valve, and a synthetic bypass artery.

34. The device of claim 31, wherein the polymer has formula (I):

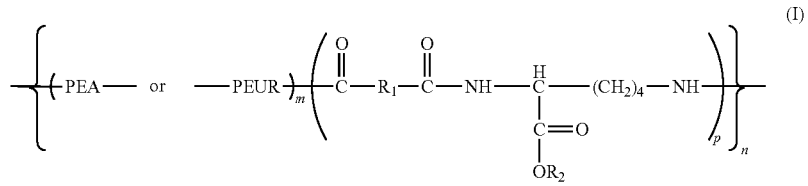

where

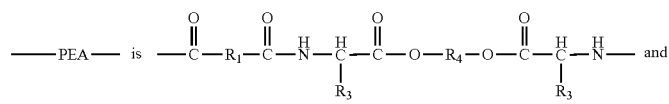

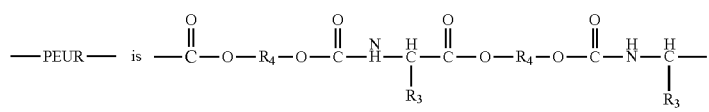

wherein n ranges from about 50 to about 150, m ranges about 0.1 to about 0.9: p ranges from about 0.9 to about 0.1;

$R_1$ is selected from $(C_2-C_{20})$alkylene and $(C_2-C_{20})$ alkenylene; $R_2$ is selected from hydrogen, $(C_6-C_{10})$aryl$(C_1-C_6)$alkyl, and t-butyl;

$R_3$ is selected from hydrogen, $(C_1-C_6)$alkyl, $(C_2-C_6)$alkenyl, $(C_2-C_6)$alkynyt and $(C_6-C_{10})$aryl$(C_1-C_6)$alkyl; and $R_4$ is selected from $(C_2-C_{20})$alkylene, $(C_2-C_{20})$alkenylene, $(C_2-C_{20})$alkyloxy, and 1,4:3,6-dianhydrohexitols of general formula (II):

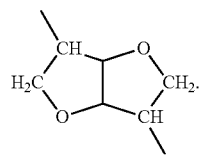

35. The device of claim 34, wherein the biodegradable, biocompatible polymer has the chemical of structural formula (I) and $R_3$ is $CH_2Ph$.

36. The device of claim 34, wherein $R_1$ is selected from —CH=CH—, —$CH_2$—CH=CH—$CH_2$—, —$(CH_2)_4$—, —$(CH_2)_6$—, and —$(CH_2)_8$—.

37. A method for promoting natural healing of endothelium damaged by mechanical intervention in an artery of a subject having Type II diabetes, comprising implanting into the artery following the mechanical intervention a the bioactive implantable stent according to claim 1 to promote natural healing of the endothelium of the artery.

38. The method of claim 37, wherein the natural healing comprises re-endothelialization of the artery.

39. The method of claim 37, wherein the mechanical intervention is angioplasty.

40. The method of claim 37, wherein the mechanical intervention is balloon angioplasty and the stent is implanted immediately following the angioplasty.

41. The method of claim 37, wherein the method comprises implanting the stent to substantially cover a section of the interior artery wall damaged by the mechanical intervention.

* * * * *